(12) United States Patent
Shidahara

(10) Patent No.: US 12,343,281 B2
(45) Date of Patent: Jul. 1, 2025

(54) HEATING IMPLEMENT

(71) Applicant: Kao Corporation, Tokyo (JP)

(72) Inventor: Yasuhiro Shidahara, Sumida-ku (JP)

(73) Assignee: Kao Corporation, Tokyo (JP)

( * ) Notice: Subject to any disclaimer, the term of this patent is extended or adjusted under 35 U.S.C. 154(b) by 383 days.

(21) Appl. No.: 17/996,811

(22) PCT Filed: Feb. 15, 2021

(86) PCT No.: PCT/JP2021/005438
§ 371 (c)(1),
(2) Date: Oct. 21, 2022

(87) PCT Pub. No.: WO2021/215089
PCT Pub. Date: Oct. 28, 2021

(65) Prior Publication Data
US 2023/0201028 A1  Jun. 29, 2023

(30) Foreign Application Priority Data

Apr. 24, 2020  (WO) .................. PCT/JP2020/017724

(51) Int. Cl.
| | | |
|---|---|---|
| *A61F 9/00* | (2006.01) | |
| *A61F 7/03* | (2006.01) | |
| *A61F 9/04* | (2006.01) | |
| *A61F 7/00* | (2006.01) | |
| *A61F 7/02* | (2006.01) | |

(52) U.S. Cl.
CPC ................. *A61F 7/034* (2013.01); *A61F 9/04* (2013.01); *A61F 2007/0004* (2013.01); *A61F 2007/0088* (2013.01); *A61F 2007/0244* (2013.01)

(58) Field of Classification Search
CPC ........................................................ A61F 9/04
See application file for complete search history.

(56) References Cited

U.S. PATENT DOCUMENTS

| | | | |
|---|---|---|---|
| 7,767,878 B2 | 8/2010 | Suzuki | |
| 9,534,810 B2 * | 1/2017 | Oka ........................ | F24V 30/00 |
| (Continued) | | | |

FOREIGN PATENT DOCUMENTS

| | | |
|---|---|---|
| CN | 101330887 A | 12/2008 |
| CN | 109620524 A | 4/2019 |
| (Continued) | | |

OTHER PUBLICATIONS

International Search Report Issued Mar. 30, 2021, in PCT/JP2021/005438, filed on Feb. 15, 2021, 3 pages.
Extended European Search Report issued Mar. 27, 2024 in European Patent Application No. 21793621.0, 10 pages.

*Primary Examiner* — Ko-Wei Lin
(74) *Attorney, Agent, or Firm* — Oblon, McClelland, Maier & Neustadt, L.L.P.

(57) ABSTRACT

A warming device including a heat generating element that contains a powder of an oxidizable metal, a powder of a carbon material, water, and a powder of a porous material other than the oxidizable metal and the carbon material. The heat generating element is a sheet material, and in the heat generating element, a ratio of the mass content of the water to the mass content of the powder of the oxidizable metal multiplied by one hundred [100×(water/powder of oxidizable metal)] is from 30 to 270.

15 Claims, 7 Drawing Sheets

(56) References Cited

U.S. PATENT DOCUMENTS

| | | | |
|---|---|---|---|
| 2006/0141882 A1* | 6/2006 | Quincy, III | C09K 5/18 427/372.2 |
| 2006/0184146 A1 | 8/2006 | Suzuki | |
| 2007/0142882 A1 | 6/2007 | Quincy, III et al. | |
| 2007/0156213 A1* | 7/2007 | Friedensohn | A61F 7/03 607/114 |
| 2008/0141437 A1 | 6/2008 | Braunecker et al. | |
| 2014/0345543 A1* | 11/2014 | Saita | A61F 7/034 122/21 |
| 2014/0373828 A1 | 12/2014 | Oka | |
| 2017/0239085 A1 | 8/2017 | Miyashita et al. | |
| 2020/0157399 A1 | 5/2020 | Homma et al. | |
| 2023/0201028 A1* | 6/2023 | Shidahara | A61F 7/034 126/263.02 |

FOREIGN PATENT DOCUMENTS

| | | |
|---|---|---|
| CN | 110678280 A | 1/2020 |
| EP | 3 165 201 A1 | 5/2017 |
| JP | 2000-342618 A | 12/2000 |
| JP | 2009-519753 A | 5/2009 |
| JP | 2010-131088 A | 6/2010 |
| JP | 2013-146554 A | 8/2013 |
| JP | 2013-146555 A | 8/2013 |
| JP | 5894761 B2 | 3/2016 |
| JP | 2019-37775 A | 3/2019 |
| JP | 2019-155055 A | 9/2019 |
| JP | 2019-162422 A | 9/2019 |
| WO | 2016/063815 A1 | 4/2016 |
| WO | WO 2019/021928 A1 | 1/2019 |
| WO | WO 2019/189850 A1 | 10/2019 |

* cited by examiner

HEATING IMPLEMENT

CROSS REFERENCE TO RELATED APPLICATIONS

This application is a National Stage entry under 35 U.S.C. § 371 of PCT/JP2021/005438, filed on Feb. 15, 2021, and PCT/JP2020/017724, filed on Apr. 24, 2020. The entire contents of both are incorporated herein by reference.

TECHNICAL FIELD

The present invention relates to a warming device.

BACKGROUND ART

Warming devices that utilize heat generated by an oxidation reaction of an oxidizable metal are used for various purposes. For example, the applicant of the present invention has previously proposed a powder-type heat generating element that includes a heat generating layer containing an oxidizable metal, a water absorbing agent, and water, and a warming device for eyes that includes the heat generating element (see Patent Literature 1). Since the heat generating element disclosed in Patent Literature 1 contains water, steam is generated as an oxidation reaction of the oxidizable metal proceeds.

Also, the applicant of the present invention has proposed a heat generating element that includes a heat generating layer containing an oxidizable metal, a water absorbing agent, and water and a water retaining layer formed of a water absorbing sheet, as well as a warming device that includes the heat generating element (see Patent Literature 2). Since the heat generating element disclosed in Patent Literature 2 contains water, steam is generated as an oxidation reaction of the oxidizable metal proceeds.

CITATION LIST

Patent Literatures

Patent Literature 1: JP 2010-131088A
Patent Literature 2: US 2014/373828A1

SUMMARY OF INVENTION

The present invention relates to a warming device.

According to an embodiment, the warming device includes a heat generating element that contains a powder of an oxidizable metal, a powder of a carbon material, water, and a powder of a porous material other than the oxidizable metal and the carbon material.

According to an embodiment, the heat generating element is a sheet material.

According to an embodiment, in the heat generating element, the ratio of the mass content of the water to the mass content of the powder of the oxidizable metal multiplied by one hundred [100×(water/powder of oxidizable metal)] is from 30 to 270.

Also, the present invention relates to another warming device.

According to an embodiment, the warming device includes a heat generating element that contains a powder of an oxidizable metal, a powder of a carbon material, water, and a powder of a porous material other than the oxidizable metal and the carbon material.

According to an embodiment, the heat generating element is a sheet material.

According to an embodiment, in the heat generating element, the ratio of the mass content of the powder of the porous material to the mass content of the powder of the oxidizable metal multiplied by one hundred [100×(powder of porous material/powder of oxidizable metal)] is from 1 to 25.

Furthermore, the present invention relates to yet another warming device.

According to an embodiment, the warming device includes a heat generating element that contains a powder of an oxidizable metal, a powder of a carbon material, water, and a powder of a porous material other than the oxidizable metal and the carbon material.

According to an embodiment, the heat generating element is a sheet material.

According to an embodiment, in the heat generating element, the ratio of the mass content of the powder of the porous material to the mass content of the water multiplied by one hundred [100×(powder of porous material/water)] is from 1 to 30.

Other features of the present invention will become apparent from the claims and the following description.

DESCRIPTION OF EMBODIMENTS

Figure 1A:
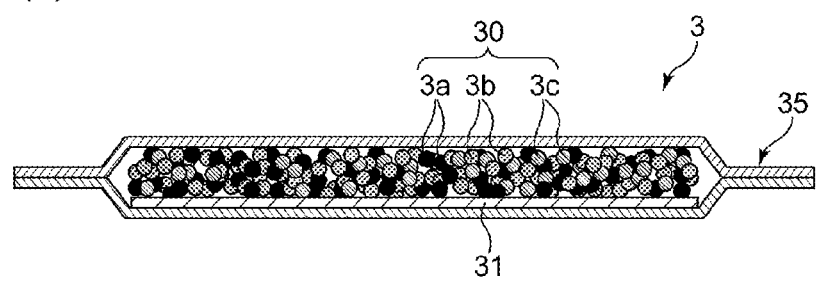
FIGS. 1(a) and 1(b) are cross-sectional views schematically showing modes of a heat generating element of a warming device.

In recent years, in response to the growing demand for warming devices, technologies for improving the heat generation characteristics and increasing the amount of steam generation, for example, have been studied.

An example of the method for improving the heat generation characteristics is to increase the content of an oxidizable metal, but this results in an increase in the production cost and an increase in the mass of the produced warming device.

Furthermore, in the powder-type heat generating element disclosed in Patent Literature 1, the constituent materials, such as the oxidizable metal, of the heat generating element may be unevenly distributed during use, thus leaving room for improvement in the heat generation characteristics and the amount of steam generation.

Furthermore, the heat generating element disclosed in Patent Literature 2 is in sheet form and has improved heat generation characteristics, but it is desired to further improve the heat generation characteristics and the amount of steam generation while reducing the production cost.

The inventor of the present invention conducted in-depth studies to improve the heat generation characteristics and the amount of steam generation and surprisingly found that, when a porous material other than the oxidizable metal and the carbon material is also contained, a warming device having good heat generation characteristics and generating a large amount of steam can be produced while suppressing the production cost.

In addition to this, the inventor of the present invention found that, when at least one of the content ratio between the oxidizable metal and water, the content ratio between the water and the porous material, and the content ratio between the oxidizable metal and the porous material satisfies a specific relationship, a warming device that has excellent heat generation characteristics and generates a large amount of steam can be produced by promoting the oxidation reaction of the oxidizable metal, while suppressing the production cost.

Therefore, the present invention relates to a warming device.

According to an embodiment, the warming device has excellent heat generation characteristics and generates a large amount of steam while suppressing the production cost.

Hereinafter, the present invention will be described based on preferred embodiments thereof.

In this specification, in the case where an upper limit value or a lower limit value, or upper and lower limit values of a certain numerical value are specified, the upper limit value and the lower limit value themselves are also included. Furthermore, even if not explicitly stated, it should be construed that all the numerical values, or numerical value ranges, equal to or smaller than the upper limit value of the certain numerical value or equal to or greater than the lower limit value thereof, or within the range between the upper and lower limit values thereof are described.

As used herein, "a", "an", and the like are to be construed as "one or more".

In view of the following disclosure in this description, it will be understood that various modifications and alterations can be made to the present invention. Accordingly, it should be appreciated that the present invention can also be implemented in embodiments that are not clearly stated in this description, as long as these embodiments do not depart from the technical scope as defined in the claims.

The entire contents of patent literatures mentioned above and below are incorporated by reference in this description as a part of the contents thereof.

The warming device of the present disclosure is used to apply warm heat to a target to be warmed, by being brought into contact with the target to be warmed when the warming device is in use.

The target to be warmed may be, for example, the skin and mucosa of the human eyes, mouth, nose, and their surrounding areas, or the skin and mucosa of the throat, face, scalp, neck, arm, shoulder, leg, knee, abdomen, back, lower back, buttock, and the like, but the target to be warmed is not limited to these, and the warming device can also be applied to other areas.

Examples of modes of the warming device of the present disclosure include, but are not limited to, the following modes (a) to (d):

(a) An eye mask form configured to be able to be held on and around the eyes;
(b) A patch form configured to be able to be held on the neck, arm, shoulder, leg, elbow, knee, forehead, abdomen, back, or lower back;
(c) A face mask form configured to be able to be held on the mouth, nose, and their surrounding areas, or the entire face; and
(d) A cup form configured to be able to be in contact with the mouth, nose, and their surrounding areas.

All disclosures in this description are applicable to all of the above-described modes (a) to (d).

The warming device of the present disclosure includes a heat generating element.

The heat generating element preferably contains (1) a powder of an oxidizable metal, (2) a powder of a carbon material, (3) a powder of a porous material, and (4) water.

The powder of the oxidizable metal has the function of causing heat generation due to an oxidation reaction with oxygen in the air and thereby making it possible to apply warm heat to the target to be warmed.

The powder of the carbon material has the function of promoting the oxidation reaction of the oxidizable metal and thereby making the heat generation efficient.

The powder of the porous material has the function of supplying water, which serves as a medium, to a reaction system when the powder of the carbon material promotes the oxidation reaction of the oxidizable metal and thereby improving the heat generation efficiency.

Note that, in the present disclosure, the oxidizable metal and the carbon material are excluded from the porous material contained in the heat generating element. This means that the heat generating element contains a porous material other than both the oxidizable metal and the carbon material.

Water has the function of facilitating the interaction between the powder of the oxidizable metal and the carbon material or the like that catalyzes the oxidation reaction.

The heat generating element preferably includes a mixture containing the above-described materials (1) to (4).

The heat generating element is preferably formed as a sheet material.

The term "sheet material" refers to a thin object having two opposing surfaces, with a small thickness between the two surfaces, and having flexibility and shape retention properties.

The sheet material has a thickness of 0.6 mm or greater, preferably 0.8 mm or greater, and more preferably 1.0 mm or greater.

Also, the sheet material has a thickness of 3.0 mm or less, preferably 2.8 mm or less, and more preferably 2.0 mm or less.

The heat generating element constituting the warming device is preferably configured to have the function of reacting with oxygen in the air to generate heat and, along with the heat generation, generating steam heated to a predetermined temperature.

In this case, the water contained in the heat generating element can partly evaporate and turn into steam as a result of the heat generation caused by the oxidation reaction of the oxidizable metal.

Examples of the form of the heat generating element include the following forms (i) and (ii).

An example of the form of the heat generating element is a form (i) in which the heat generating element is a sheet material constituted by a base sheet and a layer of a heat generative composition provided on one surface of the base sheet.

In this case, the layer of the heat generative composition is obtained by applying a paste that contains the powder of the oxidizable metal, the powder of the carbon material, the powder of the porous material, and water to one surface of the base sheet.

In the following description, this form (i) of the heat generating element will also be referred to as the "coated type".

Another example of the form of the heat generating element is a form (ii) in which the heat generating element contains, as the heat generative composition, the powder of the oxidizable metal, the powder of the carbon material, the powder of the porous material, and water, and preferably also contains a fiber material, and a mixture of these materials is molded into a sheet material by papermaking.

In the following description, this form (ii) of the heat generating element will also be referred to as the "papermade type".

For the heat generating element, one of these forms (i) and (ii) may be used as it is.

Alternatively, the heat generating element in either the form (i) or the form (ii) may be accommodated in an air-permeable enclosing material and used.

It is also preferable that the enclosing material does not allow solids to flow into and out of it.

In the case where the heat generating element is accommodated in the enclosing material, the enclosing material is separate from the heat generating element. That is to say, the enclosing material does not constitute the heat generating element.

The shape of the enclosing material is not limited to a specific shape, but is preferably a flat shape.

In the case where the enclosing material is formed into a flat shape, it is also preferable that the enclosing material is formed by bonding an air-permeable first sheet member and a second sheet member that is less air permeable than the first sheet member to each other such that the first sheet member forms one surface of the enclosing material, and the second sheet member forms the other surface of the enclosing material.

Figure 1B:
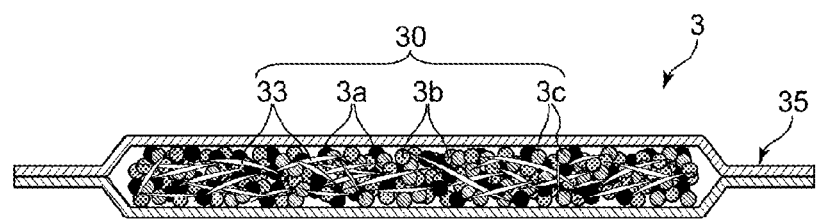

Embodiments of the above-described heat generating element are shown in FIGS. 1(a) and 1(b), for example.

FIG. 1(a) illustrates a coated type heat generating element, and FIG. 1(b) illustrates a papermade type heat generating element.

The various constituent members shown in FIGS. 1(a) and 1(b) are a heat generating element 3, a heat generative composition 30, a base sheet 31, a powder of an oxidizable metal 3a, a powder of a carbon material 3b, a powder of a porous material 3c, a fiber material 33, and an enclosing material 35.

In the heat generating element constituting the warming device, it is preferable that at least one of the content ratio between the oxidizable metal and water, the content ratio between the oxidizable metal and the porous material, and the content ratio between water and the porous material is a predetermined content ratio.

More specifically, the ratio of the mass content of the water in the in the heat generating element to the mass content of the powder of the oxidizable metal in the heat generating element multiplied by one hundred [100×(water/powder of oxidizable metal)] is preferably 30 or greater, more preferably 40 or greater, even more preferably 80 or greater, and yet even more preferably 110 or greater.

Also, the ratio of the mass content of the water in the heat generating element to the mass content of the powder of the oxidizable metal in the heat generating element multiplied by one hundred [100×(water/powder of oxidizable metal)] is preferably 270 or less, more preferably 250 or less, even more preferably 220 or less, and yet even more preferably 160 or less.

The "ratio of the mass content of the water to the mass content of the powder of the oxidizable metal multiplied by one hundred" in the present disclosure is calculated by a formula represented by "100×(mass of water [g]/mass of powder of oxidizable metal [g])".

By setting the content ratio between the oxidizable metal and water as described above, it is possible to realize heat generation characteristics equal to or superior to those of conventional warming devices even when the oxidizable metal content is lower than that in the conventional warming devices. In addition to this, it is possible to realize a reduction in the production cost of the warming device.

In the present disclosure, the "reduction in the production cost" means that the oxidizable metal content in the heat generating element can be reduced while improving the heat generation characteristics to a level equal to or higher than that of conventional warming devices.

It is more preferable that, in the heat generating element constituting the warming device, the content ratio between the powder of the oxidizable metal contained in the heat generating element and water contained in the heat generating element is set within a predetermined range according to the form of the heat generating element.

The above-described forms (i) and (ii) of the heat generating element are produced using different methods. Furthermore, different forms of the heat generating element may be used for different warming devices to be produced.

Therefore, with regard to the content ratio between the powder of the oxidizable metal contained in the heat generating element and water contained in the heat generating element, suitable ranges will be described separately below for respective cases corresponding to the forms of the heat generating element.

More specifically, in the case where the heat generating element is in the form of the coated type, the ratio of the mass content of the water in the heat generating element to the mass content of the powder of the oxidizable metal in the heat generating element multiplied by one hundred [100×(water/powder of oxidizable metal)] is preferably 80 or greater, more preferably 90 or greater, and even more preferably 110 or greater.

Also, in the case where the heat generating element is in the form of the coated type, the ratio of the mass content of the water in the heat generating element to the mass content of the powder of the oxidizable metal in the heat generating element multiplied by one hundred [100×(water/powder of oxidizable metal)] is preferably 270 or less, more preferably 220 or less, and even more preferably 160 or less.

In the case of the coated type, by setting the content ratio between the oxidizable metal and water as described above, it is possible to realize heat generation characteristics equal to or superior to those of conventional warming devices even when the oxidizable metal content is lower than that in the conventional warming devices.

By setting the oxidizable metal content and the water content so as to satisfy the more preferable range, it is possible to realize a reduction in the production cost of the warming device, in addition to the excellent heat generation characteristics described above.

Furthermore, by setting the oxidizable metal content and the water content so as to satisfy the even more preferable range, it is possible to realize an increase in the production efficiency of the warming device including the heat generating element, in addition to the excellent heat generation characteristics and the reduction in the production cost described above.

Alternatively, in the case where the heat generating element is in the form of the papermade type, the ratio of the mass content of the water in the heat generating element to the mass content of the powder of the oxidizable metal in the heat generating element multiplied by one hundred [100× (water/powder of oxidizable metal)] is preferably 30 or greater, more preferably 35 or greater, and even more preferably 40 or greater.

Also, in the case where the heat generating element is in the form of the papermade type, the ratio of the mass content of the water in the heat generating element to the mass content of the powder of the oxidizable metal in the heat generating element multiplied by one hundred [100×(water/ powder of oxidizable metal)] is preferably 80 or less, more preferably 70 or less, and even more preferably 60 or less.

In the case of the papermade type, by setting the content ratio between the oxidizable metal and water as described above, it is possible to realize heat generation characteristics equal to or superior to those of conventional warming devices even when the oxidizable metal content is lower than that in the conventional warming devices.

In the case of the papermade type, by setting the oxidizable metal content and the water content so as to satisfy the more preferable range, it is possible to realize a reduction in the production cost of the warming device, in addition to the excellent heat generation characteristics described above.

Furthermore, In the case of the papermade type, by setting the oxidizable metal content and the water content so as to satisfy the even more preferable range, it is possible to realize an increase in the production efficiency of the warming device including the heat generating element, in addition to the excellent heat generation characteristics and the reduction in the production cost described above.

Examples of the powder of the oxidizable metal constituting the heat generating element include powders of iron, aluminum, zinc, manganese, magnesium, calcium, and the like. One of these may be used alone, or two or more thereof may be used in combination.

Of these, metallic iron is preferably used in view of the ease of handling, safety, and production cost. That is to say, an iron powder is favorably used.

Examples of the iron powder include one or two or more selected from reduced iron powders and atomized iron powders.

The powder of the oxidizable metal constituting the heat generating element may be a collection of metal particles that do not have pores on the particle surface, or may be a collection of porous metal particles.

As the powder of the carbon material constituting the heat generating element, those having a function for promoting the oxidation reaction, specifically having the function of one or more of a material that retains and supplies oxygen to the oxidizable metal and a material that has a catalytic ability can be used.

Examples of such carbon materials include powders of activated carbon, such as coconut shell charcoal, charcoal powder, bituminous coal, peat, and lignite, as well as carbon black, acetylene black, graphite, and the like. One of these may be used alone, or two or more thereof may be used in combination.

Of these, a powder of activated carbon is favorably used as the powder of the carbon material because it has a good balance of oxygen supply ability and catalytic ability.

As the powder of the porous material constituting the heat generating element, a powder of a material other than the above-described oxidizable metal and carbon material can be used.

A material having the function of retaining water can be used as the porous material, and a porous inorganic compound is preferable.

Specific examples of the porous material include silicon-containing inorganic compounds such as zeolite, silica, vermiculite, perlite, and calcium silicate. One of these may be used alone, or two or more thereof may be used in combination.

Diatomaceous earth is excluded from the porous material of the present disclosure. That is to say, it is preferable that diatomaceous earth is not contained as the porous material.

In addition, the porous material may be an anhydride or a hydrate.

Pores formed in the porous material may be open-cell pores, closed-cell pores, or a combination of these.

In the case where calcium silicate is used as the porous material, examples of the calcium silicate include a gyrolite-based compound, a wollastonite-based compound, a tobermorite-based compound, and a calcium silicate hydrate-based compound. One of these may be used alone, or two or more thereof may be used in combination.

More specifically, examples of the gyrolite-based compound include gyrolite $(Ca_{16}(Si_8O_{20})_3(OH)_8 \cdot 14H_2O)$, truscottite $(Ca_{14}(Si_8O_{20})(Si_{16}O_{38})_8 \cdot 2H_2O)$, Z-phase $(Ca(Si_2O_5) \cdot 2H_2O)$, and the like.

Examples of the wollastonite-based compound include nekoite $(Ca_3(Si_6O_{15}) \cdot 8H_2O)$, okenite $(Ca_3(Si_6O_{15}) \cdot 6H_2O)$, xonotlite $(Ca_6(Si_6O_{17})(OH)_2)$, foshagite $(Ca_4(Si_3O_9)(OH)_2)$, and hillebrandite $(Ca_2(SiO_3)(OH)_2)$.

Examples of the tobermorite-based compound include tobermorite such as 14 Å tobermorite $(Ca_5(Si_6O_{18}H_2) \cdot 8H_2O)$, 11 Å tobermorite $(Ca_5(Si_6O_{18}H_2) \cdot 4H_2O)$, and 9 Å tobermorite $(Ca_5(Si_6O_{18}H_2))$, as well as quasi-crystalline calcium silicate (with a Ca/Si mole ratio of 0.8 to 2.0) and the like.

Examples of the calcium silicate hydrate-based compound include tricalcium silicate hydrate $(Ca_6(Si_2O_7)(OH)_6)$ and α-dicalcium silicate hydrate $(Ca_2(SiO_4H)(OH))$.

As the calcium silicate described above, a commercially available product may be used. For example, FLORITE® (registered trademark), which is a gyrolite-based compound, can be used as such a commercially available product.

From the viewpoint of achieving a good balance of water retention ability and water supply ability to enable the oxidation reaction of the oxidizable metal to proceed efficiently and thus obtaining a heat generating element having improved heat generation characteristics, it is preferable that the porous material contains the above-described silicon-containing inorganic compound.

In the case where the porous material contains the silicon-containing inorganic compound, the content of the silicon-containing inorganic compound in the porous material is preferably 80 mass % or greater, more preferably 90 mass % or greater, and even more preferably 100 mass % or greater, from the viewpoint of further improving the heat generation characteristics.

From the same viewpoint, it is more preferable that the silicon-containing inorganic compound is composed of one or more of silica and calcium silicate.

Furthermore, from the viewpoint of obtaining a heat generating element that has excellent heat generation characteristics and generates a large amount of steam, it is even more preferable that the silicon-containing inorganic compound is composed of calcium silicate.

Furthermore, from the viewpoint of obtaining a heat generating element having even more excellent heat generation characteristics, it is yet even more preferable to use at least one of gyrolite, xonotlite, and tobermorite, or more preferably gyrolite, as the porous material.

Next, another embodiment of the heat generating element of the warming device will be described.

In the following description, constituent elements that are different from those of the foregoing embodiments will mainly be focused on, and a description of the same constituent elements as those of the foregoing embodiments will be omitted. The description of the foregoing embodiments shall apply, as appropriate, to those constituent elements that are not specifically described in the present embodiment.

In the heat generating element of the present embodiment, it is preferable that the ratio of the mass content of the powder of the porous material to the mass content of the powder of the oxidizable metal is a predetermined ratio.

By setting the content ratio between the oxidizable metal and the porous material to a predetermined content ratio, it is possible to realize heat generation characteristics equal to or superior to those of conventional warming devices even when the oxidizable metal content is lower than that in the conventional warming devices. In addition to this, it is possible to realize a reduction in the production cost of the warming device including the heat generating element.

As is the case with the foregoing embodiments, the heat generating element of the present embodiment preferably contains a powder of an oxidizable metal, a powder of a carbon material, a powder of a porous material, and water.

Furthermore, the heat generating element of the present embodiment is preferably a sheet material.

Furthermore, the heat generating element of the present embodiment is preferably a sheet material of the coated type or the papermade type.

Furthermore, the heat generating element of the present embodiment is preferably configured to be capable of reacting with oxygen in the air to generate heat and, along with the heat generation, generating steam heated to a predetermined temperature.

In the heat generating element of the present embodiment, the ratio of the mass content of the powder of the porous material to the mass content of the powder of the oxidizable metal multiplied by one hundred [100×(powder of porous material/powder of oxidizable metal)] is preferably 1 or greater, more preferably 3 or greater, and even more preferably 5 or greater.

Also, the ratio of the mass content of the powder of the porous material to the mass content of the powder of the oxidizable metal multiplied by one hundred [100×(powder of porous material/powder of oxidizable metal)] is preferably 25 or less, more preferably 20 or less, and even more preferably 15 or less.

With the above-described ratio, the oxidation reaction of the oxidizable metal can proceed sufficiently and continuously, and thus, a warming device having excellent heat generation characteristics can be obtained. In addition to this, it is possible to realize a reduction in the production cost of the warming device.

The "ratio of the mass content of the powder of the porous material to the mass content of the powder of the oxidizable metal multiplied by one hundred" in the present disclosure is calculated by a formula represented by "100×(mass of powder of porous material [g]/mass of powder of oxidizable metal [g])".

It is also preferable that the above-described content ratio between the oxidizable metal and the porous material in the heat generating element is set within a predetermined range according to the mode of the warming device and the desired characteristics and effects to be achieved.

More specifically, for example, when the warming device is an eye mask, and a reduction in the production cost is to be achieved, from the viewpoint of continuously realizing heat generation characteristics equal to or superior to those of conventional warming devices, the ratio of the mass content of the powder of the porous material to the mass content of the powder of the oxidizable metal multiplied by one hundred [100×(powder of porous material/powder of oxidizable metal)] is preferably 1 or greater, more preferably 3 or greater, and even more preferably 5 or greater.

Also, in the case of the same form, from the viewpoint of efficiently realizing a reduction in the production cost by using a lower oxidizable metal content than that in conventional warming devices, the ratio of the mass content of the powder of the porous material to the mass content of the powder of the oxidizable metal multiplied by one hundred [100×(powder of porous material/powder of oxidizable metal)] is preferably 10 or less, more preferably 8 or less, and even more preferably 6 or less.

As another embodiment regarding the content ratio between the oxidizable metal and the porous material, for example, when the warming device is an eye mask, and an increase in the amount of steam generation is to be achieved, from the viewpoint of continuously realizing heat generation characteristics equal to or superior to those of conventional warming devices, the ratio of the mass content of the powder of the porous material to the mass content of the powder of the oxidizable metal multiplied by one hundred [100×(powder of porous material/powder of oxidizable metal)] is preferably 8 or greater, more preferably 10 or greater, and even more preferably 12 or greater.

Also, in the case of the same form, from the viewpoint of facilitating continuous generation of steam and increasing the amount of steam generation, the ratio of the mass content of the powder of the porous material to the mass content of the powder of the oxidizable metal multiplied by one hundred [100×(powder of porous material/powder of oxidizable metal)] is preferably 20 or less, more preferably 18 or less, and even more preferably 14 or less.

As another embodiment regarding the content ratio between the oxidizable metal and the porous material, for example, when the warming device is in the form of a face mask or a cup, from the viewpoint of continuously applying warmth to the target to be warmed even if the warming device is spaced apart from the target to be warmed, the ratio of the mass content of the powder of the porous material to the mass content of the powder of the oxidizable metal multiplied by one hundred [100×(powder of porous material/powder of oxidizable metal)] is preferably 3 or greater, more preferably 5 or greater, and even more preferably 6 or greater.

Also, from the viewpoint of facilitating continuous generation of steam and increasing the amount of steam generation, the ratio of the mass content of the powder of the porous material to the mass content of the powder of the oxidizable metal multiplied by one hundred [100×(powder of porous material/powder of oxidizable metal)] is preferably 15 or less, more preferably 11 or less, and even more preferably 8 or less.

Subsequently, yet another embodiment of the heat generating element of the warming device will be described.

In the following description, as is the case with the foregoing embodiments, constituent elements that are different from those of the foregoing embodiments will mainly be focused on, and a description of the same constituent elements as those of the foregoing embodiments will be omitted. The description of the foregoing embodiments shall apply, as appropriate, to those constituent elements that are not specifically described in the present embodiment.

In the heat generating element of the present embodiment, it is preferable that the ratio of the mass content of the powder of the porous material to the mass content of water is a predetermined ratio.

By setting the content ratio between water and the porous material to a predetermined content ratio, it is possible to realize heat generation characteristics equal to or superior to those of conventional warming devices even when the oxidizable metal content is lower than that in the conventional warming devices. In addition to this, it is possible to realize a reduction in the production cost of the warming device.

As is the case with the foregoing embodiments, the heat generating element of the present embodiment preferably contains a powder of an oxidizable metal, a powder of a carbon material, a powder of a porous material, and water.

Furthermore, the heat generating element of the present embodiment is preferably a sheet material.

Furthermore, the heat generating element of the present embodiment is preferably a sheet material of the coated type or the papermade type.

Furthermore, the heat generating element of the present embodiment is preferably configured to be capable of reacting with oxygen in the air to generate heat and, along with the heat generation, generating steam heated to a predetermined temperature.

In the heat generating element of the present embodiment, the ratio of the mass content of the powder of the porous material to the mass content of water multiplied by one hundred [100×(powder of porous material/water)] is preferably 1 or greater, more preferably 2 or greater, and even more preferably 3 or greater.

Also, the ratio of the mass content of the powder of the porous material to the mass content of water contained in the heat generating element multiplied by one hundred [100×(powder of porous material/water)] is preferably 30 or less, more preferably 20 or less, and even more preferably 15 or less.

With the above-described configuration, due to the pores of the porous material, an appropriate balance between the supply of water that promotes the progress of the oxidation reaction of the oxidizable metal and the supply of oxygen in the air can be achieved, and therefore, the oxidation reaction of the oxidizable metal can proceed sufficiently and continuously. Thus, a warming device 1 having excellent heat generation characteristics can be obtained. In addition to this, it is possible to realize a reduction in the production cost of the warming device.

In the heat generating element of each of the foregoing embodiments, any one of the content ratio between the oxidizable metal and water, the content ratio between the oxidizable metal and the porous material, and the content ratio between water and the porous material may be a favorable content ratio, any two of these content ratios may be favorable content ratios, or all of these content ratios may be favorable content ratios.

That is to say, the heat generating element may satisfy only a favorable content ratio between the oxidizable metal and water, may satisfy only a favorable content ratio between the oxidizable metal and the porous material, or may satisfy only a favorable content ratio between water and the porous material.

By adopting any of the above-described configurations, it is possible to realize excellent heat generation characteristics equal to or superior to those of conventional warming devices even when the oxidizable metal content is lower than that in the conventional warming devices.

Furthermore, the heat generating element may satisfy both a favorable content ratio between the oxidizable metal and water and a favorable content ratio between the oxidizable metal and the porous material, may satisfy both a favorable content ratio between the oxidizable metal and water and a favorable content ratio between water and the porous material, or may satisfy both a favorable content ratio between the oxidizable metal and the porous material and a favorable content ratio between water and the porous material.

By adopting any of the above-described combinations of the configurations, it is possible to maintain a good balance between the oxygen supply ability and the catalytic ability, and therefore, it is possible to realize even more excellent heat generation characteristics even when the oxidizable metal content is lower than that in conventional warming devices.

The heat generating element may satisfy all of a favorable content ratio between the oxidizable metal and water, a favorable content ratio between the oxidizable metal and the porous material, and a favorable content ratio between water and the porous material.

With the heat generating element satisfying all of these configurations, it is possible to maintain an even better balance between the oxygen supply ability and the catalytic ability and allow the oxidation reaction of the oxidizable metal to proceed sufficiently and continuously, and therefore, it is possible to efficiently realize yet even more excellent heat generation characteristics equal to or superior to those of conventional warming devices even when the oxidizable metal content is lower than that in the conventional warming devices.

In addition to this, it is possible to realize a further reduction in the production cost of the heat generating element and the warming device including the heat generating element.

Furthermore, it is possible to realize a further increase in the production efficiency of the heat generating element and the warming device including the heat generating element.

Hereinafter, matters that are applied to the foregoing embodiments in common will be described.

From the viewpoint of obtaining a warming device that has and can continuously exhibit excellent heat generation characteristics with high productivity, the pore diameter D1 of particles constituting the powder of the porous material is preferably 0.01 μm or greater, more preferably 0.02 μm or greater, even more preferably 0.05 μm or greater, yet even more preferably 0.1 μm or greater, and yet even more preferably 0.15 μm or greater.

Also, the pore diameter D1 of particles constituting the powder of the porous material is preferably 5 μm or less, more preferably 1 μm or less, even more preferably 0.8 μm or less, yet even more preferably 0.5 μm or less, and yet even more preferably 0.3 μm or less.

In the case where calcium silicate is used as the porous material, the pore diameter D1 of particles of the calcium silicate is more preferably 0.02 μm or greater, even more preferably 0.05 μm or greater, yet even more preferably 0.1 μm or greater, and yet even more preferably 0.15 μm or greater.

In the case where calcium silicate is used as the porous material, the pore diameter D1 of particles of the calcium silicate is more preferably 0.8 μm or less, even more preferably 0.5 μm or less, and yet even more preferably 0.3 μm or less.

By setting the pore diameter D1 of the porous material within the above-described range, it is possible to efficiently transfer water retained by the powder of the porous material to the oxidizable metal, and therefore to further improve the heat generation characteristics.

The above-described effects become more pronounced by setting the pore diameter D1 within the more preferable range, and become even more pronounced by setting the pore diameter D1 within the even more preferable range.

The above-described pore diameter D1 of the porous material can be measured using, for example, a mercury porosimetry method specified in JIS R1655.

Note that, when two or more types of porous materials are blended, the pore diameter of the mixture of the porous materials is measured, and the measured value is used as the pore diameter D1.

Measurement of the pore diameter using the mercury porosimetry method specified in JIS R1655 can be performed in the following manner, for example. First, 0.02 to 0.1 g of a powder of a porous material to be measured is placed in a measurement cell as a measurement sample, the measurement cell is then set in a mercury porosimeter (e.g., AutoPore IV9500 manufactured by Micromeritics), and the cumulative pore volume V (cm³/g) of the measurement sample when the pressure P at which mercury is injected is increased within a predetermined range is measured. Next, a pore volume distribution is obtained by plotting the converted pore diameter D (μm) obtained through conversion according to an equation (A) below on the horizontal axis and the relationship with the log differential pore volume (dV/d (log$_{10}$D); cm³/g) on the vertical axis. That is to say, a pore volume distribution is obtained in which the converted pore diameter D is plotted on the horizontal axis and the pore volume obtained by differentiating the cumulative pore volume V by the logarithmic value the pore diameter D is plotted on the vertical axis.

$$D = 4\gamma \cos \theta / P \quad \text{(A)}$$

(γ: surface tension of mercury, θ: angle of contact, P: pressure at which mercury is injected)

The above-described measurement is performed in an environment at 22° C. and 65% RH. The surface tension γ of mercury is 480 dyn/cm, the angle of contact θ is 140°, and the pressure P at which mercury is injected is within a range from 0 psia (0 MPa) to 60000 psia (413.685 MPa). Based on a distribution curve of the converted pore diameter D obtained under the above-described measurement conditions, the cumulative total value of the converted pore diameters D within a range from 0.0018 to 100 μm is obtained as the cumulative pore volume V (mL/g), and the median of the pore diameter on the distribution curve is obtained as the pore diameter D1 (μm) of the present disclosure.

The amount of oil absorption of the powder of the porous material is preferably 300 mL/100 g or greater, more preferably 350 mL/100 g or greater, and even more preferably 400 mL/100 g or greater.

Also, the amount of oil absorption of the powder of the porous material is preferably 900 mL/100 g or less, more preferably 800 mL/100 g or less, and even more preferably 700 mL/100 g or less.

With the amount of oil absorption within the above-described range, water contained in the heat generating element is sufficiently retained by the particles of the porous material, and the water retained by the porous material can be even more efficiently transferred to the oxidizable metal. Thus, the heat generation characteristics can be continuously and efficiently improved.

The amount of oil absorption of the porous material can be measured according to JIS K5010-13-2. Specifically, 1 to 5 g of a powder sample to be measured is placed on a center portion of a measurement plate, boiled linseed oil is added dropwise from a burette, 4 to 5 drops at a time, onto the center of the sample, and each time boiled linseed oil is added dropwise, the entire sample is sufficiently kneaded using a palette knife. The dropwise addition of boiled linseed oil and the kneading of the sample are repeated, and after the entire sample becomes a stiff putty-like mass, the entire sample is kneaded each time one drop of boiled linseed oil is added. The end point is when the sample after one drop of boiled linseed oil is added thereto is in a state of being able to be wound into a spiral shape using the palette knife, and at this point in time, the amount (mL) of boiled linseed oil that has been added dropwise is read from a scale. However, if the sample cannot be wound into a spiral shape, the end point is immediately before the sample suddenly softens after adding one drop of boiled linseed oil thereto, and at this point in time, the amount (mL) of boiled linseed oil that has been added dropwise is read from the scale.

The amount of powder sample to be used for the measurement is determined in accordance with the specification in JIS K5010-13-2 after performing a preliminary test and confirming the approximate value of the amount of oil absorption in advance.

Furthermore, when two or more types of porous materials are blended, the amount of oil absorption of the mixture of the porous materials is measured.

The amount (mL/100 g) of oil absorption of the present disclosure is calculated by converting the amount (mL) of boiled linseed oil that has been added dropwise, which is obtained according to the above-described method, into an amount per 100 g of the measured powder sample.

In the case where the powder of the oxidizable metal is constituted by particles having pores on their surface, it is preferable that the pore diameter D2 of the particles constituting the powder of the oxidizable metal is smaller than the pore diameter D1 of the powder of the porous material.

With this configuration, due to the difference in capillary force, water retained by the porous material can be even more efficiently transferred to the oxidizable metal, and thus, the heat generation characteristics can be further improved.

More specifically, the pore diameter D2 of particles constituting the powder of the oxidizable metal is preferably 0.001 μm or greater, more preferably 0.003 μm or greater, and even more preferably 0.006 μm or greater.

The pore diameter D2 of particles constituting the powder of the oxidizable metal is preferably 0.07 μm or less, more preferably 0.05 μm or less, and even more preferably 0.01 μm or less.

Setting the pore diameter D2 within the above-described range makes it possible for water retained by the porous material to be efficiently drawn into the oxidizable metal due to the difference in capillary force, and consequently, it is possible to further promote the oxidation reaction of the oxidizable metal and thus even further improve the heat generation characteristics.

Such a powder of an oxidizable metal can be produced using a method disclosed in EP 3626367A1, for example.

The above-described pore diameter D2 of the powder of the oxidizable metal can be measured using, for example, the mercury porosimetry method specified in JIS R1655. Specifically, 0.02 to 0.1 g of a powder of an oxidizable metal is placed in a measurement cell as a measurement sample, the measurement cell is then set in a mercury porosimeter (e.g., AutoPore IV9500 manufactured by Micromeritics), and the cumulative pore volume V (cm³/g) of the measurement sample when the pressure P at which mercury is injected is increased within a predetermined range is obtained. Next, a pore volume distribution is obtained by plotting the converted pore diameter D (μm) obtained through conversion according to an equation (A) below on the horizontal axis and the relationship with the log differential pore volume (dV/d (log$_{10}$D); cm³/g) on the vertical axis. That is to say, a pore volume distribution is obtained in which the converted pore diameter D is plotted on the horizontal axis and the pore volume obtained by differentiating the cumulative pore volume V by the logarithmic value the pore diameter D is plotted on the vertical axis.

$$D=4\gamma \cos \theta/P \qquad (A)$$

(γ: surface tension of mercury, θ: angle of contact, P: pressure at which mercury is injected)

The above-described measurement is performed in an environment at 22° C. and 65% RH. The surface tension γ of mercury is 480 dyn/cm, the angle of contact θ is 140°, and the pressure P at which mercury is injected is within a range from 0 psia (0 MPa) to 60000 psia (413.685 MPa). Based on a distribution curve of the converted pore diameter D obtained under the above-described measurement conditions, the cumulative total value of the converted pore diameters D within a range from 0.0018 to 100 μm is obtained as the cumulative pore volume V (mL/g), and the median of the pore diameter on the distribution curve is obtained as the pore diameter D2 (μm) of the present disclosure.

From the viewpoint of enabling steam to be continuously generated and the oxidation reaction to moderately proceed, it is also preferable that a water absorbing resin is also provided in or near the heat generating element.

From the viewpoint of enabling steam to be continuously generated and the oxidation reaction to moderately proceed, and also increasing the production efficiency even more by preventing the constituent materials from unintentionally falling out, in the case where the water absorbing resin is also provided, it is more preferable that an enclosing material is also provided and a layer containing a powder of the water absorbing resin is disposed between the heat generative composition of the heat generating element and the enclosing material.

The above-described forms can each be applied to both the coated type and the papermade type.

The water absorbing resin provided in or near the heat generating element can absorb excess water present in the heat generating element. As a result, the heat generation characteristics can be improved as a result of the oxidation reaction of the oxidizable metal proceeding efficiently, and water retained by the water absorbing resin and the heat generating element can also be continuously released as steam. Therefore, pleasant warmth can be applied to a user of the warming device.

In the case where the water absorbing resin is also provided in or near the heat generating element, an example mode of presence of the water absorbing resin is a mode in which a powder of the water absorbing resin is present mixed with the powder of the oxidizable metal, the powder of the carbon material, the powder of the porous material, and water in the heat generative composition of the heat generating element. In this case, the powder of the water absorbing resin constitutes a part of the heat generating element.

Alternatively, another example mode of presence of the water absorbing resin is a mode in which a layer containing a powder of the water absorbing resin is present adjacent to the heat generating element. In this case, the layer containing the powder of the water absorbing resin is separate from the heat generating element.

Examples of the mode in which the layer containing the powder of the water absorbing resin is present adjacent to the heat generating element include: (a) a mode in which a single layer formed by sandwiching the powder of the water absorbing resin between two moisture-permeable sheets is provided; (b) a mode in which the powder of the water absorbing resin is disposed so as to form a single layer while being in contact with the heat generative composition constituting the heat generating element, with no other members provided therebetween; and (c) a mode in which a stack structure constituted by a first water absorbing resin layer in which particles of the powder of the water absorbing resin are arranged adjacent to each other into a layer and a second water absorbing resin layer that is adjacent to the first water absorbing resin layer and is formed by sandwiching the powder of the water absorbing resin between two moisture-permeable sheets is disposed adjacent to the heat generative composition constituting the heat generating element, with no other members provided therebetween.

That is to say, in any of the cases (a) to (c) described above, it is preferable that the heat generative composition constituting the heat generating element is disposed between the base sheet and the layer containing the powder of the water absorbing resin.

Further alternatively, yet another example mode of presence of the water absorbing resin is a mode in which a layer containing the powder of the water absorbing resin is provided as the base sheet and is present adjacent to the heat generative composition of the heat generating element. In this case, the powder of the water absorbing resin constitutes a part of the heat generating element.

Preferably, the layer containing the powder of the water absorbing resin is formed by sandwiching the water absorbing resin between two moisture-permeable sheets. In this case, it is also preferable that the heat generative composition of the heat generating element is disposed in contact with an outer surface of one of the moisture-permeable sheets.

In the case where the layer containing the powder of the water absorbing resin is provided as the base sheet, it is preferable that the layer containing the powder of the water absorbing resin is accommodated in the enclosing material together with the heat generating element in order to prevent the constituent materials from unintentionally falling out.

In the case where the enclosing material is provided, it is also preferable that the enclosing material is formed by bonding an air-permeable first sheet member and a second sheet member that is less air permeable than the first sheet member to each other such that the first sheet member forms one surface of the enclosing material and the second sheet member forms the other surface of the enclosing material.

Preferably, the enclosing material has a flat shape.

In the case where the layer containing the powder of the water absorbing resin is provided as the base sheet and the enclosing material is provided, it is more preferable that the layer containing the powder of the water absorbing resin and the air-permeable first sheet member of the enclosing material are arranged facing each other.

Figure 2A:
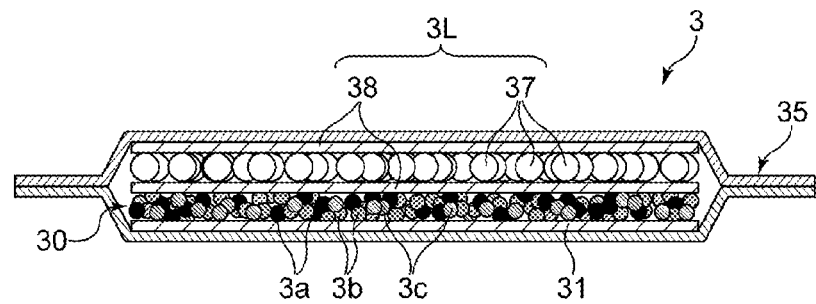
FIGS. 2(a) to 2(c) are cross-sectional views schematically showing modes of arrangement of the heat generating element and a water absorbing resin layer of the warming device.
Figure 2B:
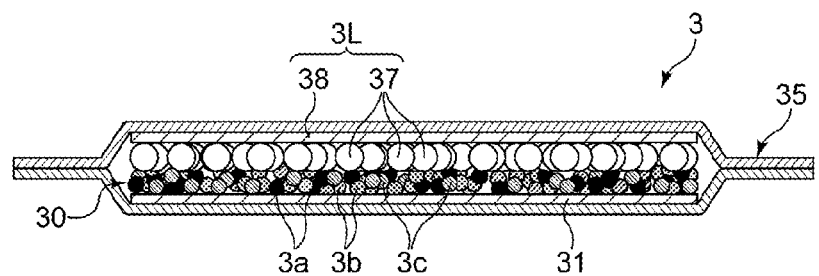
Figure 2C:
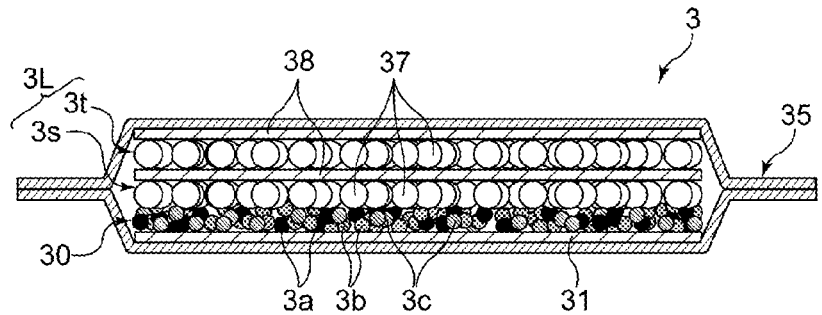

With regard to the mode of presence of the heat generating element and the water absorbing resin, FIGS. 2(a) to 2(c) show examples of the form in which the layer containing the powder of the water absorbing resin is present adjacent to the heat generating element.

In all of the embodiments shown in FIGS. 2(a) to 2(c), a layer 3L (hereinafter also referred to as "water absorbing resin layer 3L") containing a powder of a water absorbing resin 37 is disposed between the heat generative composition 30 of the heat generating element 3 and the enclosing material 35.

Note that, although the heat generating element 3, the water absorbing resin layer 3L, and the enclosing material 35 shown in FIGS. 2(a) to 2(c) are generally depicted as having different thicknesses, they are shown as such only for the sake of convenience of description, and the actual heat generating element 3, water absorbing resin layer 3L, and enclosing material 35 in each of the forms shown in FIGS. 2(a) to 2(c) may have the same thickness or different thicknesses.

More specifically, in the case where the water absorbing resin layer 3L is provided, it is preferable that the water absorbing resin layer 3L is formed by sandwiching the water absorbing resin 37 between two moisture-permeable sheets 38 as shown in FIG. 2(a). In this case, it is also preferable that the water absorbing resin layer 3L is in contact with the heat generative composition 30 constituting the heat generating element 3 via a corresponding one of the moisture-permeable sheets 38.

More specifically, it is preferable that the heat generative composition 30 constituting the heat generating element 3 is disposed between the base sheet 31 and the water absorbing resin layer 3L.

With this configuration, the warming device can generate more steam than conventional warming devices by continuously releasing steam while continuously exhibiting the excellent heat generation characteristics, and therefore, it is possible to allow the target to be warmed, such as the eyes, nose, or throat, to continuously perceive both pleasant warmth and moisture.

The above-described configuration of the water absorbing resin layer is advantageous, for example, in that, by being adopted in a warming device preferably in the form of an eye mask or a patch, it can allow an applied area, such as the eyes and surrounding area, of the user to continuously perceive warmth and can thereby make the user feel more relaxed.

Alternatively, it is also preferable that, as shown in FIG. 2(b), the water absorbing resin layer 3L has a configuration in which the water absorbing resin 37 is disposed so as to form a layer while being in contact with the heat generative composition 30 constituting the heat generating element 3, with no other members provided therebetween.

More specifically, it is preferable that the heat generative composition 30 constituting the heat generating element 3 is disposed between the base sheet 31 and the water absorbing resin layer 3L.

With this configuration, the warming device can generate even more steam than conventional warming devices, and therefore has the advantage of increasing the amount of steam generation even more and being able to allow the target to be warmed, such as the eyes, nose, mouth, or throat, to perceive both pleasant warmth and moisture.

The above-described configuration of the water absorbing resin layer is advantageous, for example, in that, by being adopted in a warming device preferably in the form of a face mask, it can allow a wide area, that is, the mouth, nose, and surrounding areas, of the user to perceive warmth and moisture and can thereby make the user feel more relaxed.

Further alternatively, it is also preferable that, as shown in FIG. 2(c), the water absorbing resin layer 3L has a stack structure constituted by a first water absorbing resin layer 3s in which the water absorbing resin 37 is disposed adjacent to the heat generative composition 30 constituting the heat generating element 3, with no other members provided therebetween, and a second water absorbing resin layer 3t that is adjacent to the first water absorbing resin layer 3s and is formed by sandwiching the water absorbing resin 37 between the two moisture-permeable sheets 38.

More specifically, it is preferable that the heat generative composition 30 constituting the heat generating element 3 is disposed between the base sheet 31 and the water absorbing resin layer 3L.

In the embodiment shown in FIG. 2(c), the water absorbing resin layer 3L has a stack structure in which the first water absorbing resin layer 3s and the second water absorbing resin layer 3t are arranged in contact with each other.

With this configuration, the warming device can generate a large amount of steam in a relatively short time by allowing the exothermic reaction of the heat generating element to proceed efficiently, and therefore, it is possible to allow the target to be warmed, such as the eyes, nose, mouth, or throat, to quickly perceive warmth and moisture.

The above-described configuration of the water absorbing resin layer is advantageous, for example, in that, by being adopted in a warming device preferably in the form of a cup, it can intensively apply warmth and moisture to the mouth, nose, and surrounding areas of the user in a short time.

Figure 3:
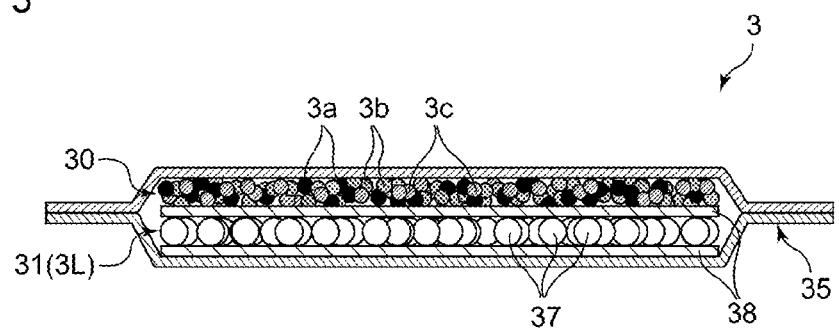
FIG. 3 is a cross-sectional view schematically showing another mode of arrangement of the heat generating element and the water absorbing resin layer of the warming device.

With regard to the mode of presence of the heat generating element and the water absorbing resin, FIG. 3 shows an example of the other form in which the layer containing the powder of the water absorbing resin is present adjacent to the heat generative composition.

In an embodiment shown in FIG. 3, the water absorbing resin layer 3L is disposed between the heat generative composition 30 of the heat generating element 3 and the enclosing material 35.

It is preferable that, as shown in FIG. 3, the water absorbing resin layer 3L is formed by sandwiching the water absorbing resin 37 between the two moisture-permeable sheets 38.

Also, it is preferable that, as shown in FIG. 3, the heat generative composition 30 of the heat generating element 3 is disposed in contact with one surface of a corresponding one of the moisture-permeable sheets 38. In this case, it is also preferable that the water absorbing resin layer 3L is used as the base sheet 31 of the heat generating element 3.

As shown in FIG. 3, in the case where the water absorbing resin layer 3L is provided as the base sheet 31 and the flat enclosing material 35 is provided, it is more preferable that the water absorbing resin layer 3L and the air-permeable first sheet member of the enclosing material are arranged facing each other.

With this configuration, the warming device can generate more steam than conventional warming devices by continuously releasing steam while continuously exhibiting the excellent heat generation characteristics, and therefore, it is possible to allow the target to be warmed, such as the eyes, nose, or throat, to continuously perceive both pleasant warmth and moisture.

The above-described configuration of the water absorbing resin layer is advantageous, for example, in that, by being adopted in a warming device preferably in the form of an eye mask or a patch, it can allow an applied area, such as the eyes and surrounding area, of the user to continuously perceive warmth and can thereby make the user feel more relaxed.

In the case where the water absorbing resin layer is disposed adjacent to the heat generating element, the water absorbing resin layer is preferably formed as a sheet material.

Specific examples of the water absorbing resin include one or more of starch, cross-linked carboxylmethylated cellulose, as well as polyacrylic acid, its salts, and polyacrylic acid salt graft polymers, such as polymers or copolymers of acrylic acid or alkali metal salts of acrylic acid.

A sodium salt can be used as the polyacrylic acid salt.

With regard to the shape of the water absorbing resin, particles having a spherical shape, a clump shape, a grape cluster shape, or a fibrous shape, or a combination of these shapes, for example, can be used.

The water absorbing resin is preferably a powder constituted by a collection of particles.

As the moisture-permeable sheet, for example, a fiber sheet such as tissue paper, absorbent paper, or a nonwoven fabric, a mesh sheet, or the like can be used.

The moisture-permeable sheet is preferably air permeable.

From the viewpoint of obtaining a warming device with favorable heat generation characteristics by appropriately controlling the oxidation reaction, the particle size of particles constituting the powder of the oxidizable metal is preferably 1 µm or greater, and more preferably 10 µm or greater.

From the same viewpoint, the particle size of particles constituting the powder of the oxidizable metal is preferably 200 µm or less, and more preferably 100 µm or less.

From the viewpoint of obtaining a warming device with favorable heat generation characteristics by allowing the powder of the carbon material to sufficiently exhibit the catalytic ability for the oxidation reaction, the particle size of particles constituting the powder of the carbon material is preferably 1 µm or greater, and more preferably 10 µm or greater.

From the same viewpoint, the particle size of particles constituting the powder of the carbon material is preferably 200 µm or less, and more preferably 100 µm or less.

From the viewpoint of obtaining a warming device with favorable heat generation characteristics by appropriately controlling the water retention and water supply, the particle size of particles constituting the powder of the porous material is preferably 1 µm or greater, and more preferably 10 µm or greater.

From the same viewpoint, the particle size of particles constituting the powder of the porous material is preferably 200 µm or less, and more preferably 100 µm or less.

In the case where the water absorbing resin is used as a powder, with regard to the particle size of particles constituting the powder, particle sizes within a range commonly used in the art can be used.

The particle size of each of the above-described materials can be, for example, a median diameter measured by a laser diffraction/scattering method using a laser diffraction/scattering particle size distribution analyzer (manufactured by HORIBA, Ltd. (model: LA-950V2)).

In the case where the heat generating element is a paper-made type sheet material that contains a fiber material, natural and synthetic fiber materials can be used as the fiber material without particular limitations.

Examples of the natural fiber materials include plant fibers (cotton, kapok, wood pulp, non-wood pulp, peanut protein fiber, corn protein fiber, soybean protein fiber, mannan fiber, rubber fiber, hemp, manila hemp, sisal hemp, New Zealand flax, Apocynum venetum L., palm, rush, straw, etc.), animal fibers (sheep's wool, goat's hair, mohair, cashmere, alpaca, angora, camel, vicuna, silk, down, down, feather, algin fiber, chitin fiber, casein fiber, etc.), and mineral fibers (asbestos etc.). One of these fiber materials may be used alone, or a plurality of fiber materials selected from these fiber materials may be used in combination.

Examples of the synthetic fiber materials include semi-synthetic fibers (acetate, triacetate, oxidized acetate, promix, rubber chloride, rubber hydrochloride, etc.), synthetic polymer fibers (polyesters such as nylon, aramid, polyvinyl alcohol, polyvinyl chloride, polyvinylidene chloride and polyethylene terephthalate, polyacrylonitrile, acrylic, polyethylene, polypropylene, polystyrene, polyurethane, rayon, viscose rayon, cupra, etc.), metal fibers, carbon fibers, glass fibers, and the like. One of these fiber materials may be used alone, or a plurality of fiber materials selected from these fiber materials may be used in combination.

Of the above-listed fiber materials, it is preferable to use at least one of wood pulp, cotton, and polyester as the fiber material in order to improve the heat generation characteristics by achieving both uniform dispersion of the oxidizable metal and good oxygen permeability, which is achieved by securing gaps.

The average fiber length of the fiber material is preferably 0.5 mm or greater, and more preferably 2 mm or greater.

Also, the average fiber length of the fiber material is preferably 10 mm or less, and more preferably 5 mm or less.

The average fiber length of the fiber material is determined as follows: Fifty or more fibers of the fiber material are used as measurement targets. In a state in which one end portion of each fiber is fixed to a horizontal plate and the fiber is allowed to hang down under its own weight, the fiber length is measured using a fastening ruler. Alternatively, each fiber is fastened to a microscope slide, and the fiber length is measured using a microscope. An arithmetic mean value of the obtained measurement results is used as the average fiber length of the fiber material.

From the viewpoint of facilitating the steam generation caused by the heat generating element generating heat, it is preferable that the heat generating element contains an electrolyte.

Examples of the electrolyte contained in the heat generating element include one or two or more of salts of alkali metals or alkaline earth metals with phosphoric acid or sulfuric acid and chlorides or hydroxides of alkali metals or alkaline earth metals.

Of these, preferably, one or two or more of tripotassium phosphate, potassium hydroxide, sodium chloride, and potassium chloride are used as the electrolyte in view of their excellent chemical stability and low production costs.

The electrolyte may be used as, for example, a powder, or a liquid in which the electrolyte is dissolved or dispersed in a liquid solvent such as water.

The heat generating element may be composed only of the powder of the oxidizable metal, the powder of the carbon material, the powder of the porous material, and water, and the fiber material if necessary, or may also contain in the heat generative composition, in addition to the various powders and water, and the fiber material if necessary, another powder other than the powder of the oxidizable metal, the powder of the carbon material, and the powder of the porous material.

Examples of the other powder include one or two or more of the above-described water absorbing resins and electrolytes.

From the viewpoint of further improving the heat generation characteristics and the amount of steam generation, the content ratio of the other powder in the heat generating element is preferably 20 mass % or less, and more preferably 10 mass % or less, with respect to the total mass of all the powders constituting the heat generating element.

From the viewpoint of further improving the heat generation characteristics and the amount of steam generation, the ratio of the total mass of the powder of the oxidizable metal, the powder of the carbon material, and the powder of the porous material to the total mass of all the powders constituting the heat generating element is preferably 80 mass % or greater, and more preferably 90 mass % or greater.

In the case where a water absorbing resin is contained as the other powder, the mass of the powder of the water absorbing resin is based on its absolute dry mass.

In the warming device that is configured as described above, the oxidation reaction of the oxidizable metal can be promoted as a result of the heat generating element in the form of a sheet material also containing the porous material other than the oxidizable metal and the carbon material, and at least one of the content ratio between the oxidizable metal and water, the content ratio between the oxidizable metal and the porous material, and the content ratio between water and the porous material being appropriately set. Consequently, a warming device that shows a high integrated amount of sensible heat, which is expressed as the integral of temperature over the duration of heat generation, and therefore has excellent heat generation characteristics can be obtained.

Furthermore, excellent heat generation characteristics can be realized even when the oxidizable metal content is lower than that in conventional warming devices, and therefore, a warming device having heat generation characteristics equal to or superior to those of conventional warming devices can be produced while suppressing the cost.

Furthermore, by appropriately setting at least one of the content ratio between the oxidizable metal and water, the content ratio between the oxidizable metal and the porous material, and the content ratio between water and the porous material, it is possible to obtain a warming device that has excellent heat generation characteristics and generates a large amount of steam while suppressing the production cost, irrespective of the form of the warming device.

In general, the oxidation reaction of the oxidizable metal can be affected by the amounts of water and oxygen that are present around the metal powder.

More specifically, if an excessively large amount of water is present around the metal powder, the water forms a barrier and makes it harder for oxygen to come into contact with the oxidizable metal, and as a result, the oxidation reaction will not continue, or the start of the oxidation reaction will be delayed.

On the other hand, if the amount of water that is present around the metal powder is excessively small, the oxidizable metal can more readily come into contact with oxygen, but the water-mediated interaction with the carbon material or the like that catalyzes the oxidation reaction is less likely to occur, and as a result, the oxidation reaction will not sufficiently continue and it is difficult to realize desired heat generation characteristics.

In this regard, it is supposed that, as a result of using the porous material, sufficient water can be retained in the pores of the porous material and the water retained by the porous material is continuously supplied to the oxidizable metal in appropriate amounts, and thus, the necessary amounts of water and oxygen for the oxidation reaction to continuously proceed are secured.

In particular, as the oxidation reaction proceeds, pores are formed in the surface of the oxidizable metal and the oxidizable metal becomes porous. Therefore, a capillary force created between the porous material and the oxidizable metal causes water to be continuously supplied from the porous material to the oxidizable metal. Accordingly, the oxidation reaction proceeds continuously, a certain amount of heat generation is maintained for a long period of time, and thus, a warming device that has further improved heat generation characteristics can be obtained.

This can be made more pronounced by using preferably the silicon-containing inorganic compound described above, more preferably calcium silicate, and even more preferably at least one of gyrolite, xonotlite, and tobermorite, as the porous material.

Furthermore, due to the improved heat generation characteristics, water contained in the heat generating element evaporates as the heat is generated, and a larger amount of steam is generated than in conventional warming devices. Therefore, the warming device also has the advantage of increasing the amount of steam generation and being able to make the user of the warming device continuously perceive pleasant warmth.

Furthermore, the above-described improvements in the heat generation characteristics and the amount of steam generation can be easily achieved independent of the presence or absence of the air-permeable enclosing material and other sheet members constituting the warming device, or the degree of air resistance of the air-permeable enclosing material and other sheet members constituting the warming device.

It is preferable that the warming device includes a main body and the heat generating element included in the main body.

It is also preferable that the main body is shaped to cover the target to be warmed when the warming device is in use.

It is preferable that the warming device includes a topsheet located on a side that is close to the target to be warmed and a backsheet located on a side that is far from the target to be warmed.

More specifically, it is preferable that the warming device includes a topsheet located on a side that is close to the user's skin and a backsheet located on a side that is far from the user's skin.

It is preferable that the main body of the warming device is constituted by the topsheet and the backsheet.

It is preferable that the heat generating element is held between the topsheet and the backsheet that constitute the main body.

It is also preferable that the heat generating element is held between the topsheet and the backsheet while being accommodated in the air-permeable enclosing material.

In the case where the enclosing material is formed by the first sheet member and the second sheet member, it is preferable that the air-permeable first sheet member is disposed on the side that is close to the target to be warmed, or more specifically, on the side that is close to the user's skin. That is to say, it is preferable that the first sheet member is disposed facing the topsheet.

In the case where the enclosing material is formed by the first sheet member and the second sheet member, it is preferable that the second sheet member that is less air permeable than the first sheet member is disposed on the side that is far from the target to be warmed, or more specifically, on the side that is far from the user's skin. That is to say, it is preferable that the second sheet member is disposed facing the backsheet.

It is also preferable that the warming device is configured to generate steam heated to a predetermined temperature. Thus, warm heat can be applied to the target to be warmed and surrounding area.

Hereinafter, an embodiment of the warming device will be described with reference to the drawings.

FIGS. 4 to 7 show, as an embodiment of the warming device, a warming device in the form of a so-called eye mask.

That is to say, the present disclosure includes use of the warming device as an eye mask and a method of using the warming device as an eye mask.

In the following description, constituent elements that are different from those of the foregoing embodiments will mainly be focused on, and the same constituent elements as those of the foregoing embodiments are denoted by the same reference numerals and a description thereof will be omitted. The description of the foregoing various configurations shall apply, as appropriate, to those constituent elements that are not specifically described in the present embodiment.

The warming device of the present embodiment is configured to be able to be held on and around the eyes. This warming device is used by being brought into contact with human eyes serving as a target to be warmed so as to cover the eyes when the warming device is in use and apply warm heat to the eyes and surrounding area.

The warming device is configured to generate steam heated to a predetermined temperature and can thus apply warm heat to the eyes and surrounding area, which serve as the target to be warmed.

It is preferable that the warming device of the present embodiment includes a main body that is shaped to cover the eyes of the user when the warming device is in use and that is elongated in the lateral direction, as well as the heat generating element included in the main body.

Furthermore, it is also preferable that the warming device of the present embodiment includes a pair of earloop portions that are attached to the main body. The earloop portions enable the eyes of the user to be kept covered.

In the following description of the present embodiment, a direction that corresponds to the longitudinal direction of the warming device will also be referred to as "lateral direction", and a direction perpendicular to the lateral direction will also be referred to as "length direction".

Figure 4:
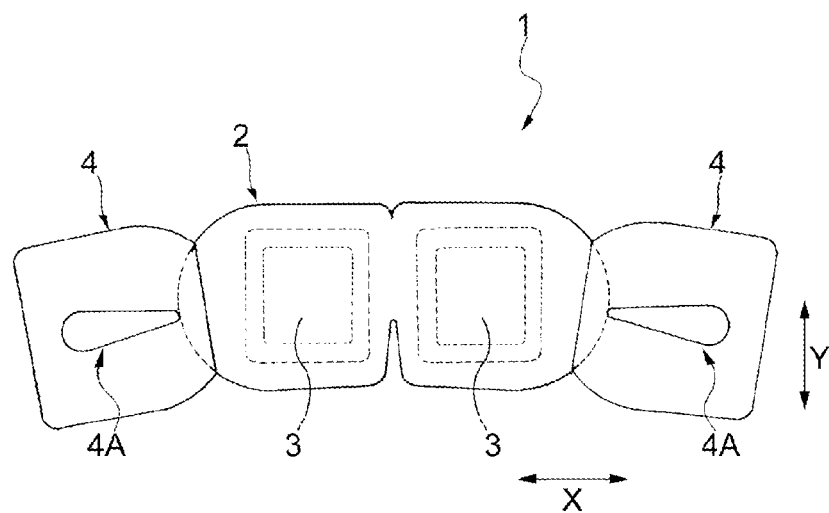
FIG. 4 is a plan view schematically showing an embodiment of the warming device.

In FIG. 4, by way of example, the warming device of the present embodiment is shown as a warming device 1 having a main body 2, heat generating elements 3, a lateral direction X, and a length direction Y.

In the warming device 1 shown in FIG. 4, the earloop portions 4 are provided in opposing outer end regions of the main body 2 in the lateral direction X and can be opened outward in the lateral direction X. Thus, a state in which the eyes of the user are covered by the main body 2 can be maintained by placing the earloop portions 4 around the respective ears of the user.

From the viewpoint of improving the ease of wearing, an elastic sheet is preferably used as a sheet member that constitutes the earloop portions 4.

Figure 5:
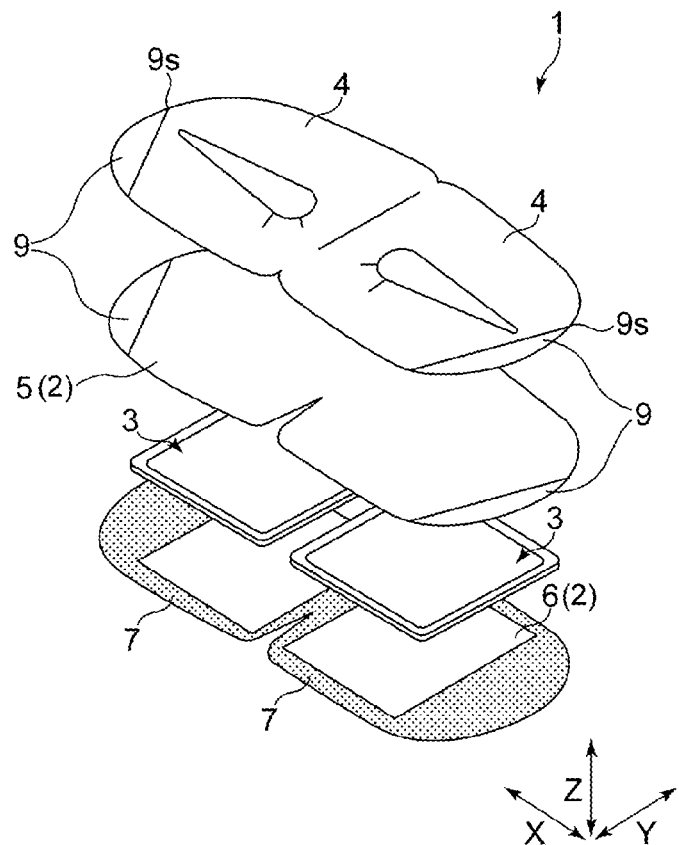
FIG. 5 is an exploded perspective view schematically showing the warming device shown in FIG. 4.

FIG. 5 shows an exploded perspective view of the warming device 1 of the present embodiment.

Figure 6:
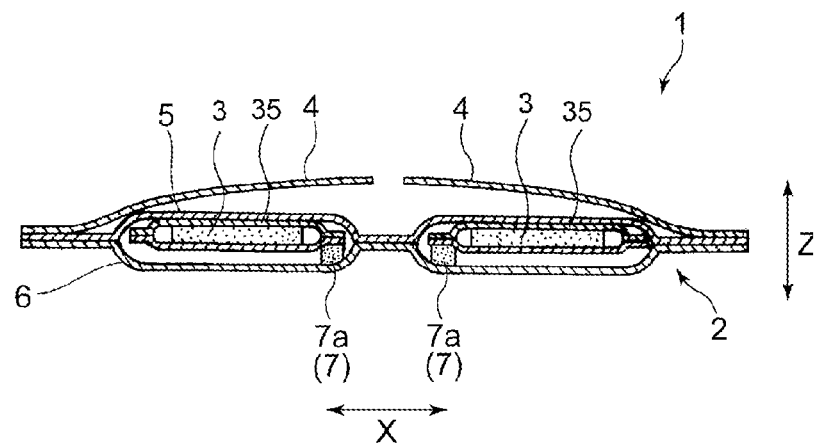
FIG. 6 is a schematic diagram showing a cross section of the warming device shown in FIG. 4 taken along a lateral direction that is a longitudinal direction of the warming device.

FIG. 6 shows a cross-sectional view of the warming device 1 taken along the lateral direction X.

The main body 2 included in the warming device 1 shown in FIGS. 5 and 6 has a flat shape and includes a topsheet 5 located on a side that is close to the user's skin and a backsheet 6 located on a side that is far from the user's skin.

The topsheet 5 constitutes a surface that includes an area that comes into contact with the target to be warmed, such as human eyes, mouth, or nose, when the warming device 1 is in use.

The backsheet 6 constitutes a surface that is far from the user's skin, and forms an outer surface of the warming device 1. That is to say, in FIGS. 5 and 6, the upper side in the paper plane is the side that is close to the user's skin, and the lower side in the paper plane is the side that is far from the user's skin.

The topsheet 5 and the backsheet 6 shown in FIGS. 5 and 6 are superposed and joined to each other using an adhesive 7 such as a hot melt adhesive, and thus, the two heat generating elements 3 are accommodated between the two sheets 5 and 6 while being spaced apart from each other in the lateral direction X.

That is to say, in the present embodiment, the heat generating elements 3 are not detachable from the main body 2.

It is preferable that the heat generating elements 3 are held between the topsheet 5 and the backsheet 6 that constitute the main body 2.

It is preferable that, of the topsheet 5 and the backsheet 6, at least the topsheet 5 is made using an air-permeable fiber sheet.

The fiber sheet is a collection of a plurality of constituent fibers that are formed and retained in the shape of a sheet by at least one of entanglement, fusion bonding, and bonding of the plurality of constituent fibers.

A detailed description of the sheets 5 and 6 will be given later.

The cross-sectional view of FIG. 6 shows a state in which the heat generating elements 3 are fixed.

As shown in FIG. 6, it is also preferable that the heat generating elements 3 are each accommodated in an enclosing material 35 that is formed by bonding a plurality of sheet members to each other through heat sealing or the like and that is air permeable.

In this case, it is also preferable that the heat generating elements 3 are held between the topsheet 5 and the backsheet 6 while being accommodated in the respective air-permeable enclosing materials 35.

Preferably, the enclosing materials 35 have a flat shape. In the case, it is also preferable that the enclosing materials 35 are each formed by bonding an air-permeable first sheet member and a second sheet member that is less air permeable than the first sheet member to each other such that the first sheet member forms one surface of the enclosing material 35 and the second sheet member forms the other surface of the enclosing material 35.

In the case where the enclosing materials 35 are each formed by the first sheet member and the second sheet member, it is preferable that the air-permeable first sheet member is disposed on the side that is close to the user's skin. That is to say, it is preferable that the first sheet member is disposed facing the topsheet 5.

In the case where the enclosing materials 35 are each formed by the first sheet member and the second sheet member, it is preferable that the second sheet member that is less air permeable than the first sheet member is disposed on the side that is far from the user's skin. That is to say, it is preferable that the second sheet member is disposed facing the backsheet 6.

In the case where the warming device 1 includes the enclosing materials 35, it is preferable that, as shown in FIG. 6, a portion of an outer surface of each enclosing material 35 is fixed to an inner surface of the backsheet 6 of the warming device 1 via an adhesive fixing portion 7a formed by the adhesive 7, and the other portions of the outer surface of the enclosing material 35 are not fixed to the backsheet 6.

The adhesive fixing portions 7a shown in FIG. 6 are provided in a center region of the warming device 1 in the lateral direction X and extend in the length direction Y of the warming device 1.

With this configuration, when the warming device 1 is in use, the heat generating elements 3 can be placed on the target to be warmed with a good fit, and thus, warm heat can be efficiently applied to the target to be warmed.

Returning to FIG. 5, it is preferable that, as shown in FIG. 5, the earloop portions 4 are made using a sheet member, and insertion portions 4A extending in the lateral direction X are formed in the sheet member.

The insertion portions 4A are holes through which the ears are passed when the earloop portions 4 are placed around the ears.

Alternatively, the insertion portions 4A may be through slits or the like through which the ears can be passed.

Figure 7:
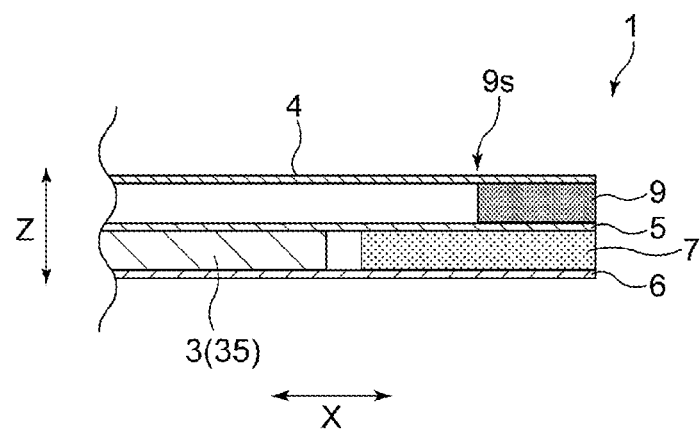
FIG. 7 is a schematic diagram showing an enlarged cross section of the warming device shown in FIG. 5.

As shown in FIGS. 5 and 7, the earloop portions 4 are joined to an outer surface of the topsheet 5 of the main body 2 in opposing outer end regions of the earloop portions 4 in the lateral direction X, and thus, joined regions 9 where the main body 2 is joined to the earloop portions 4 are formed.

The joined regions 9 also function as bending portions that are bent along joined end portion 9s when the earloop portions 4 are opened outward.

FIG. 7 is a cross-sectional view showing a form of the joined regions 9 of the warming device 1 of the present embodiment.

It is preferable that each of the joined regions 9 shown in FIGS. 5 and 7, where the main body 2 and a corresponding one of the earloop portions 4 are joined to each other, has a substantially semielliptical shape, with the main body 2 and the earloop portion 4 being continuously joined to each other from the joined end portion 9s, which is the inner end of the joined region 9 in the lateral direction X, to the outer end of the main body 2 in the lateral direction X.

It is preferable that, as shown in FIG. 7, the joined region 9 is formed as a result of the topsheet 5 of the main body 2 and the earloop portion 4 being joined to each other.

It is preferable that the joined region 9 also functions as the bending portion that is bent along the joined end portion 9s when the earloop portion 4 is opened outward.

The joined regions 9 shown in FIGS. 5 and 7 are formed through continuous joining, but instead may be formed through intermittent joining.

Figure 8:
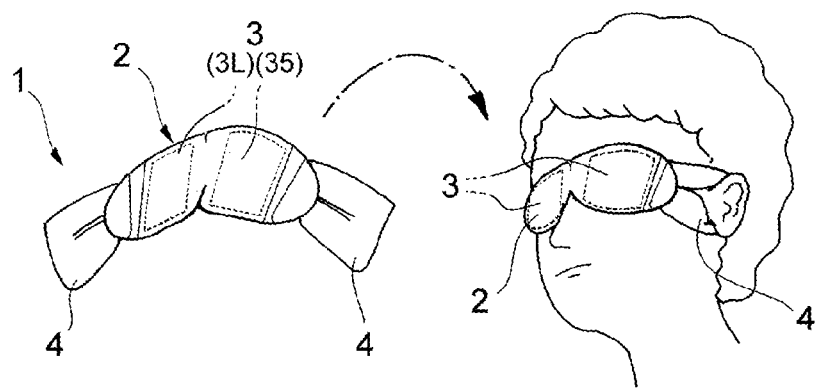
FIG. 8 schematically shows a state in which the warming device shown in FIG. 4 is used.

As an example of the method of using the warming device 1 in the form of the eye mask shown in FIGS. 4 to 7, the warming device 1 can be used by being held on the ears using the earloop portions 4 as shown in FIG. 8.

This form of use makes it possible for steam and warm heat that are generated from the warming device 1 to be uniformly applied to the user's eyes and surrounding area independent of the posture (e.g., supine position, sitting position, or the like) of the user. This is advantageous in that the form of use of the warming device 1 becomes more versatile.

Figure 9:
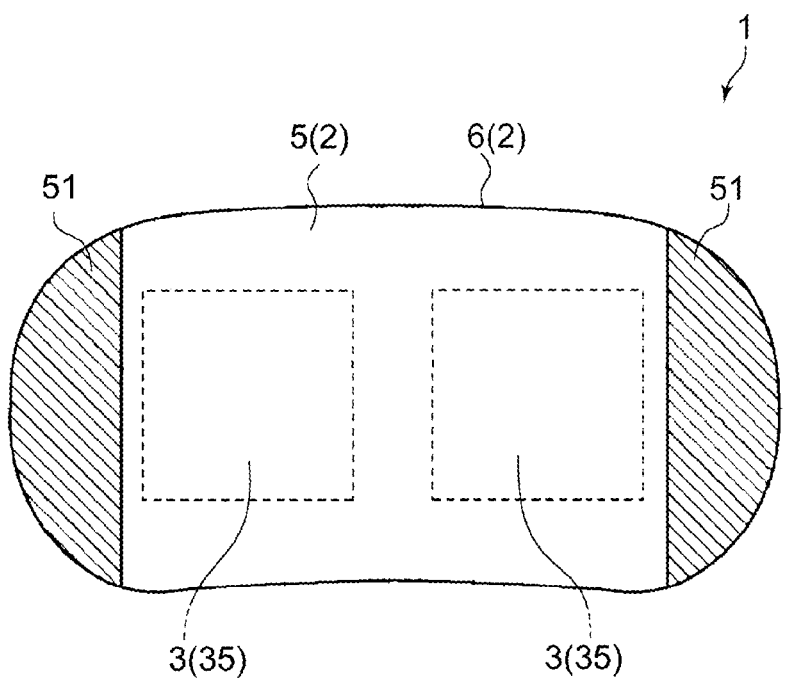
FIG. 9 is a plan view schematically showing another embodiment of the warming device.

Hereinafter, another embodiment of the warming device 1 will be described with reference to FIG. 9. FIG. 9 shows, as an embodiment of the warming device 1, a warming device in the form of a so-called patch.

That is to say, the present disclosure includes use of the warming device in the form of a patch and a method of using the warming device in the form of a patch.

In the following description, constituent elements that are different from those of the foregoing embodiments will mainly be focused on, and the same constituent elements as those of the foregoing embodiments are denoted by the same reference numerals and a description thereof will be omitted. The description of the foregoing various configurations shall apply, as appropriate, to those constituent elements that are not specifically described in the present embodiment.

FIG. 9 shows, as an embodiment in which the warming device 1 is in the form of a patch.

It is preferable that the warming device 1 of the present embodiment includes a main body 2 having a topsheet 5 that constitutes a skin-facing surface when the warming device 1 is in use and a backsheet 6 that constitutes a non-skin-facing surface when the warming device 1 is in use, as well as heat generating elements 3 included in the main body 2.

It is preferable that the heat generating elements 3 are held between the topsheet 5 and the backsheet 6 that constitute the main body 2.

It is also preferable that the heat generating elements 3 are held between the topsheet 5 and the backsheet 6 that constitute the main body 2, while being accommodated in respective air-permeable enclosing materials 35.

In the present embodiment, it is preferable that a pressure-sensitive adhesive portion 51 is provided on a part of the region or the entire region of the outer surface of the topsheet 5, which constitutes the skin-facing surface.

The pressure-sensitive adhesive portion 51 is used to hold the warming device 1 on an area to which warm heat and steam generated from the warming device 1 are to be applied.

With the pressure-sensitive adhesive portion 51 being provided, the warming device 1 can be used by being attached directly to the user's skin or by being attached to the clothing of the user, and thus, the warming device 1 can be easily held on a predetermined area that is the target to be warmed.

Furthermore, in order to make the pressure-sensitive adhesive portion exhibit the pressure-sensitive adhesive properties at a desired timing, a base material, such as a film, that covers the pressure-sensitive adhesive portion may also be provided.

Figure 10:
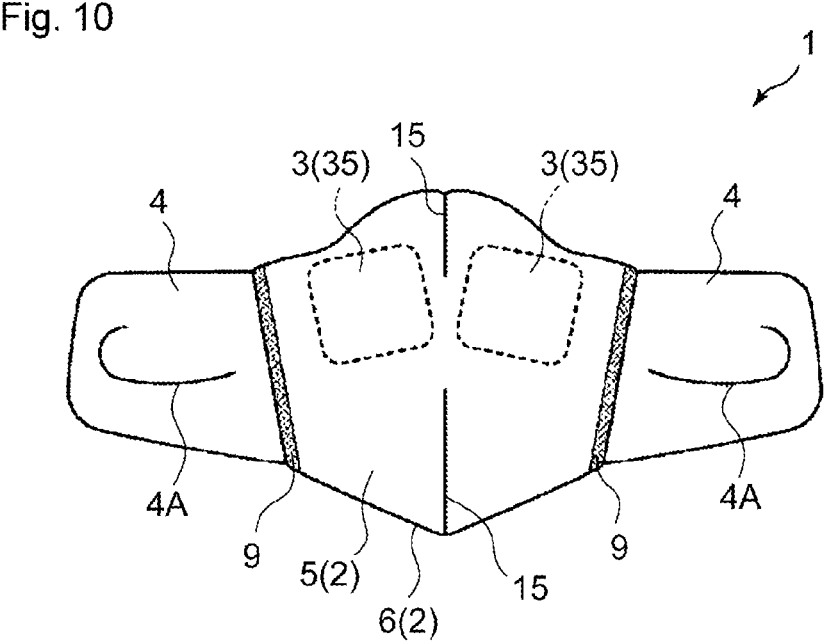
FIG. 10 is a plan view schematically showing yet another embodiment of the warming device.

Hereinafter, yet another embodiment of the warming device 1 will be described with reference to FIG. 10. FIG. 10 shows, as an embodiment of the warming device, a warming device in the form of a so-called face mask.

That is to say, the present disclosure includes use of the warming device as a face mask and a method of using the warming device as a face mask.

In the following description as well, constituent elements that are different from those of the foregoing embodiments will mainly be focused on, and the same constituent elements as those of the foregoing embodiments are denoted by the same reference numerals and a description thereof will be omitted. The description of the foregoing various configurations shall apply, as appropriate, to those constituent elements that are not specifically described in the present embodiment.

FIG. 10 shows an embodiment in which the warming device 1 is in the form of a face mask.

It is preferable that the warming device 1 of the present embodiment includes a main body 2 that covers at least one of the mouth and the nose of the user when the warming device 1 is in use, as well as heat generating elements 3 included in the main body 2.

In addition to this, it is preferable that the warming device 1 of the present embodiment includes a pair of earloop portions 4 that are provided at left and right ends of the main body 2. The earloop portions enable at least one of the mouth and the nose of the user to be kept covered.

The earloop portions 4 of the present embodiment are each made using a sheet member.

It is preferable that an insertion portion 4A is formed in a center region of each earloop portion 4.

It is preferable that heat generating elements 3 are held between a topsheet 5 and a backsheet 6 that constitute the main body 2.

It is also preferable that the heat generating elements 3 are held between the topsheet 5 and the backsheet 6 that constitute the main body 2, while being accommodated in respective air-permeable enclosing materials 35.

It is preferable that, as shown in FIG. 10, the warming device 1 of the present embodiment has a folding line 15 at a position corresponding to the bridge of the nose of the user.

The folding line 15 of the present embodiment is provided in a center region of the main body 2 of the warming device 1 in the lateral direction.

With this configuration, when the warming device 1 in the form of the face mask is used, the topsheet 5 can be made to conform to the protruding shape of the nose, with the folding line 15 serving as a flexible axis, and brought into close contact with the nose, and thus, a gap is less likely to be created between the warming device 1 and the target to be warmed, and the warming and moisturizing effect can be improved.

Alternatively, depending on the intended use or the like, the warming device 1 may have a flat shape without the folding line 15.

As an example of the method of using the warming device 1 of the present embodiment, the warming device 1 can be used by being held on the ears using the earloop portions 4.

Figure 11:
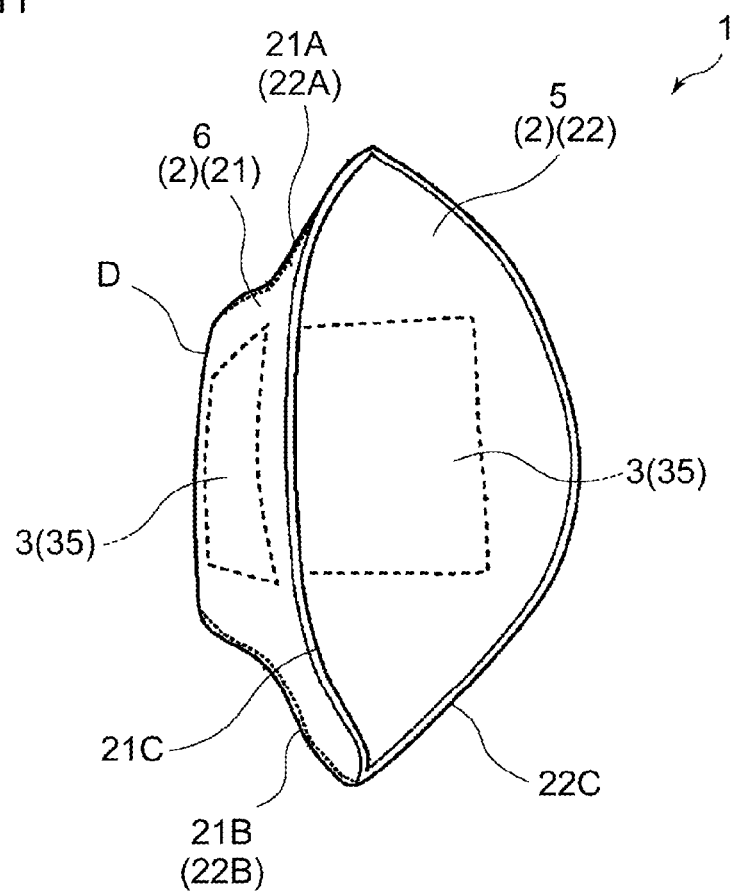
FIG. 11 is a perspective view schematically showing yet another embodiment of the warming device.

Hereinafter, yet another embodiment of the warming device 1 will be described with reference to FIG. 11. FIG. 11 shows, as an embodiment of the warming device, a warming device in the form of a so-called cup.

That is to say, the present disclosure includes use of the warming device in the form of a cup and a method of using the warming device in the form of a cup.

In the following description as well, constituent elements that are different from those of the foregoing embodiments will mainly be focused on, and the same constituent elements as those of the foregoing embodiments are denoted by the same reference numerals and a description thereof will be omitted. The description of the foregoing various configurations shall apply, as appropriate, to those constituent elements that are not specifically described in the present embodiment.

FIG. 11 shows an embodiment in which the warming device 1 is in the form of a cup.

It is preferable that the warming device 1 of the present embodiment includes a main body 2 that covers at least one of the mouth and the nose of the user when the warming device 1 is in use, as well as heat generating elements 3 included in the main body 2.

Depending on the intended use, the warming device 1 of the present embodiment may or may not include earloop portions that enable at least one of the mouth and the nose of the user to be kept covered.

It is preferable that, as shown in FIG. 11, the warming device 1 of the present embodiment has the main body 2 constituted by a first panel portion 21 and a second panel portion 22 that are connected to each other, the second panel portion 22 having substantially the same shape as the first panel portion 21.

It is preferable that, in the present embodiment, the two panel portions 21 and 22 are both formed in a fan shape, and tapered portions of the two panel portions 21 and 22 are connected to each other.

It is preferable that both the first panel portion 21 and the second panel portion 22 are made using a single continuous topsheet 5 and a single continuous backsheet 6, and heat generating elements 3 are held between the topsheet 5 and the backsheet 6.

It is also preferable that the heat generating elements 3 are held between the topsheet 5 and the backsheet 6 that constitute the main body 2, while being accommodated in respective air-permeable enclosing materials 35.

It is preferable that the warming device 1 of the present embodiment has a boundary line D that serves as a flexible axis for bending the main body 2 at a connecting portion between the first panel portion 21 and a second panel portion 22.

It is preferable that, in the present embodiment, the first panel portion 21 and the second panel portion 22 are shaped to be line-symmetrical to each other, where the boundary line D is the line of symmetry.

The warming device 1 of the present embodiment is bent along the boundary line D such that two halves of the topsheet 5 face each other, and furthermore, a first side edge 21A of the first panel portion 21 and a first side edge 22A of the second panel portion 22 are laid on top of each other and joined to each other, and also a second side edge 21B of the first panel portion 21 and a second side edge 22B of the second panel portion 22 are laid on top of each other and joined to each other.

In the two panel portions 21 and 22, a third side edge 21C of the first panel portion 21 and a third side edge 22C of the second panel portion 22 that are located on the outer sides are not joined to each other and together form an opening of the cup shape. It is preferable that this opening is open to such an extent that the opening can cover the mouth and nose of the user.

Thus, a bottomed cylindrical cup-like warming device having a bottom at the position of the boundary line D and the vicinity thereof is formed. The outer surface of this cup-like warming device is formed by the backsheet 6, and the inner surface thereof is formed by the topsheet 5.

The cup-like warming device of the present embodiment does not have earloop portions. In this case, it is preferable that a main body of the bottomed cylindrical cup-like warming device has dimensions that allow the main body to be held in a human hand. That is to say, it is preferable that the cup-like warming device is configured such that the main body can be held in a human hand.

When in use, the cup-like warming device can be used by, for example, holding the main body in a human hand with the opening of the cup-like warming device kept in the vicinity of the nose and mouth of the user.

The various types of sheet members that can be used as the earloop portions, the topsheet and the backsheet, as well as the base sheet, the enclosing materials, and the moisture-permeable sheet may each independently be determined as appropriate by taking into consideration the air permeability, moisture permeability, texture, elasticity, strength, leakage prevention of the materials constituting the heat generative composition, and other properties of these components.

For example, a fiber sheet such as a non-woven fabric, a woven fabric, or paper, a resin foamed sheet, a metal sheet, or a combination thereof can be used as the sheet members.

Each sheet member may have a single structure composed only of a single sheet member including one or more layers, or a stack structure in which two or more types of sheet members are stacked.

Melt-blown nonwoven fabrics are preferably used as sheet members that are highly air permeable and moisture permeable.

Air-through nonwoven fabrics and thermal bonded nonwoven fabrics are preferably used as sheet members that are used in order to improve the texture.

Air-through nonwoven fabrics, spunbonded nonwoven fabrics, thermal bonded nonwoven fabrics, and the like that contain synthetic fibers made of, for example, polyester such as polyethylene terephthalate, polyethylene, or polypropylene are used as sheet members that are used in order to realize elasticity.

Spunbonded nonwoven fabrics, spunlaced nonwoven fabrics, needle punched nonwoven fabrics, chemically bonded nonwoven fabrics, and the like are preferably used as sheet members that are used in order to impart strength.

In addition to or instead of the above-described nonwoven fabrics, it is also possible to use nonwoven fabrics whose surface has been treated with silicone, a surfactant, or the like, foamed sheets made of a thermoplastic resin such as polyethylene or polyurethane, and the like.

Furthermore, these sheet members can also be made to realize desired properties by using a mixture of a plurality of types of fibers of different raw materials, different fiber diameters, different fiber crimp levels, and the like, or by using a plurality of sheet members in combination.

The earloop portions, the topsheet and the backsheet, as well as the base sheet, the enclosing materials, and the moisture-permeable sheet may each independently have a single structure composed only of a single sheet member including one or more layers, or a stack structure in which two or more types of sheet members are stacked.

As described above, it is preferable to use a fiber sheet as the topsheet.

From the viewpoint of improving the production efficiency of the warming device, at least one of a needle punched nonwoven fabric, an air-through nonwoven fabric, a spun bonded nonwoven fabric, and a chemically bonded nonwoven fabric can be favorably used.

In the case where fiber sheets such as nonwoven fabrics are used as the topsheet and the backsheet, it is preferable that both the topsheet and the backsheet are air permeable. The term "air permeable" means that the air resistance as measured according to JIS P8117: 2009 is 10000 sec/100 mL or less. The air resistance as measured according to JIS P8117 is defined as the time for 100 mL of air to pass through an area of 6.42 $cm^2$ under normal temperature and pressure.

More specifically, the topsheet and the backsheet each independently have an air resistance of preferably 0.01 sec/100 mL or greater, and more preferably 0.03 sec/100 mL or greater.

The air resistance is measured according to JIS P8117: 2009. When the air resistance takes a small value, it means that it does not take time for the air to pass through the topsheet, and thus the air permeability is high.

By using a topsheet having such air resistance, it is possible to efficiently apply warm heat and steam to the target to be warmed and efficiently control the oxidation reaction of the oxidizable metal to thereby obtain a warming device having desired heat generation characteristics.

In the case where an air-permeable enclosing material is provided and the enclosing material has an air-permeable first sheet member and a second sheet member that is less air permeable than the first sheet member, the air resistance of the first sheet member constituting the enclosing material is preferably 20 sec/100 mL or greater, more preferably 30 sec/100 mL or greater, and even more preferably 40 sec/100 mL or greater.

Also, the air resistance of the first sheet member is preferably 25000 sec/100 mL or less, more preferably 15000 sec/100 mL or less, and even more preferably 10000 sec/100 mL or less.

As the first sheet member having the above-described air resistance, for example, a resin film having a plurality of through holes or a film obtained by uniaxially or biaxially stretching a sheet made of a resin composition containing polyethylene and a filler such as calcium carbonate can be used. The air resistance can be changed as appropriate by adjusting the degree of stretching.

For example, EP 1939240A1 discloses a sheet that can be used as the first sheet member.

In the case where an air-permeable enclosing material is provided and the enclosing material has an air-permeable first sheet member and a second sheet member that is less air permeable than the first sheet member, the air resistance of the second sheet member constituting the enclosing material is preferably 10000 sec/100 mL or greater, and more preferably 25000 sec/100 mL or greater. From the viewpoint of realizing sufficient and appropriate heat generation characteristics and applying sufficient steam to the target to be warmed, it is even more preferable that the second sheet member is air impermeable.

The term "air impermeable" means that the air resistance as measured according to JIS P8117: 2009 is 80000 sec/100 mL or greater.

As the second sheet member having the above-described air resistance, for example, a resin film having less through holes than the first sheet member or having no through holes can be used.

In the case where an air-permeable enclosing material is provided and the enclosing material has an air-permeable first sheet member and a second sheet member that is less air permeable than the first sheet member, the water vapor transmission rate of moisture of the first sheet member as measured according to JIS Z0208 is preferably 480 g/(m²·24 h) or greater, more preferably 720 g/(m²·24 h) or greater, and even more preferably 960 g/(m²·24 h) or greater.

Also, the water vapor transmission rate of moisture of the first sheet member as measured according to JIS Z0208 is preferably 5000 g/(m²·24 h) or less, more preferably 4750 g/(m²·24 h) or less, and even more preferably 4500 g/(m²·24 h) or less.

Furthermore, the water vapor transmission rate of moisture of the second sheet member as measured according to JIS Z0208 is preferably 480 g/(m²·24 h) or less, more preferably 240 g/(m²·24 h) or less, and even more preferably 0 g/(m²·24 h).

By setting the water vapor transmission rates of moisture of the first sheet member and the second sheet member each independently within the above-described ranges, it is possible to realize sufficient and appropriate heat generation characteristics and apply sufficient steam to the target to be warmed.

As the sheet members that satisfy such water vapor transmission rates of moisture, for example, similar sheet members to those described above with respect to the air resistance can be used.

In the case where a fiber sheet is used as the topsheet, the basis weight of the topsheet is preferably 10 g/m² or greater, more preferably 30 g/m² or greater, and even more preferably 50 g/m² or greater.

The basis weight of the topsheet is preferably 200 g/m² or less, more preferably 130 g/m² or less, and even more preferably 100 g/m² or less.

In the case where a fiber sheet is used as the backsheet, from the viewpoint of improving heat retention properties and printability, it is preferred that the backsheet has a lower basis weight than the topsheet.

More specifically, the basis weight of the backsheet is preferably 10 g/m² or greater, and more preferably 20 g/m² or greater.

The basis weight of the backsheet is preferably 100 g/m² or less, and more preferably 80 g/m² or less.

In the case where the topsheet and the backsheet each have a stack structure, it is sufficient that the basis weight of the entire sheet is within the above-described range.

The term "moisture permeable" as used for a moisture-permeable sheet means that the water vapor transmission rate of moisture of the sheet as measured according to JIS Z0208 is 2000 g/(m²·24 h) or greater.

Specifically, the water vapor transmission rate of moisture of the moisture-permeable sheet as measured according to JIS Z0208 is preferably 2000 g/(m²·24 h) or greater, more preferably 2500 g/(m²·24 h) or greater, and even more preferably 3000 g/(m²·24 h) or greater.

A sheet that is moisture permeable as described above can be suitably used as the moisture-permeable sheet of the water absorbing resin layer. In the case where a plurality of moisture-permeable sheets are used, the values of the water vapor transmission rate of moisture of the plurality of moisture-permeable sheets may be the same or different.

In the case where the warming device has earloop portions, the form of the earloop portions is not limited to the sheet-like member shown in FIGS. 4 and 5 as long as the main body can be fixed to the eyes of the user.

For example, instead of the earloop portions that are made using a sheet member, earloop portions that are made using a strap-like member or earloop portions that are made using a thread- or band-like member may be adopted.

From the viewpoint of enhancing the fit of the warming device, the earloop portions 4 are preferably made using an elastic body such as a rubber and stretchable.

As the form of the heat generating elements of the warming devices according to the embodiments shown in FIGS. 4, 9, 10, and 11, a form in which two heat generating elements are held spaced apart from each other was described; however, there is no particular limitation on the form of the heat generating elements as long as warmth can be applied to the target to be warmed and surrounding area.

For example, a single heat generating element of a shape and a size that can cover the target to be warmed and surrounding area may be held between the topsheet and the backsheet, or three of more heat generating elements may be held between the topsheet and the backsheet.

Also, the heat generating elements shown in FIGS. 5 and 6 are configured such that only a portion of each heat generating element is fixed in the center region of the warming device in the lateral direction; however, the form of the heat generating elements is not limited to this form.

For example, a heat generating element and the backsheet may be continuously or intermittently joined to each other using an adhesive in a center region in the lateral direction and a region other than the center region, or a heat generating element may be joined to the backsheet by applying an adhesive to the entire surface of a portion of the backsheet where the heat generating element is disposed.

Although the present invention has been described based on preferred embodiments thereof, the present invention is not limited to the embodiments above.

With respect to the embodiments of the present disclosure described above, warming devices as described below are also disclosed.

<1>

A warming device including a heat generating element that contains a powder of an oxidizable metal, a powder of a carbon material, water, and a powder of a porous material other than the oxidizable metal and the carbon material,
  wherein the heat generating element is a sheet material, and
  in the heat generating element, the ratio of the mass content of the water to the mass content of the powder of the oxidizable metal multiplied by one hundred [100×(water/powder of oxidizable metal)] is from 30 to 270.

<2>

A warming device including a heat generating element that contains a powder of an oxidizable metal, a powder of a carbon material, water, and a powder of a porous material other than the oxidizable metal and the carbon material,
  wherein the heat generating element is a sheet material, and
  in the heat generating element, the ratio of the mass content of the powder of the porous material to the mass content of the powder of the oxidizable metal multiplied by one hundred [100×(powder of porous material/powder of oxidizable metal)] is from 1 to 25.

<3>

A warming device including a heat generating element that contains a powder of an oxidizable metal, a powder of a carbon material, water, and a powder of a porous material other than the oxidizable metal and the carbon material,
 wherein the heat generating element is a sheet material, and
 in the heat generating element, the ratio of the mass content of the powder of the porous material to the mass content of the water multiplied by one hundred [100×(powder of porous material/water)] is from 1 to 30.

<4>

The warming device as set forth in any one of clauses <1> to <3>, wherein the ratio of the mass content of the powder of the porous material to the mass content of the powder of the oxidizable metal multiplied by one hundred [100×(powder of porous material/powder of oxidizable metal)] is preferably 1 or greater, more preferably 3 or greater, and even more preferably 5 or greater.

<5>

The warming device as set forth in any one of clauses <1> to <4>, wherein the ratio of the mass content of the powder of the porous material to the mass content of the powder of the oxidizable metal multiplied by one hundred [100×(powder of porous material/powder of oxidizable metal)] is preferably 25 or less, more preferably 20 or less, and even more preferably 15 or less.

<6>

The warming device as set forth in any one of clauses <1> to <5>,
 wherein the ratio of the mass content of the powder of the porous material to the mass content the water multiplied by one hundred [100×(powder of porous material/water)] is preferably 1 or greater, more preferably 2 or greater, and even more preferably 3 or greater.

<7>

The warming device as set forth in any one of clauses <1> to <6>,
 wherein the ratio of the mass content of the powder of the porous material to the mass content of the water multiplied by one hundred [100×(powder of porous material/water)] is preferably 30 or less, more preferably 20 or less, and even more preferably 15 or less.

<8>

The warming device as set forth in any one of clauses <1> to <7>,
 wherein the heat generating element is accommodated in an air-permeable enclosing material, and
 a layer containing a powder of a water absorbing resin is disposed between the heat generating element and the enclosing material.

<9>

The warming device as set forth in clause <8>,
 wherein the layer is formed by sandwiching the powder of the water absorbing resin between two moisture-permeable sheets.

<10>

The warming device as set forth in clause <9>
 wherein the water vapor transmission rate of moisture of the moisture-permeable sheets as measured according to JIS Z0208 is preferably 2000 g/(m²·24 h) or greater, more preferably 2500 g/(m²·24 h) or greater, and even more preferably 3000 g/(m²·24 h) or greater.

<11>

The warming device as set forth in any one of clauses <8> to <10>,
 wherein one surface of the enclosing material is preferably formed by an air-permeable first sheet member, and
 the other surface of the enclosing material is preferably formed by a second sheet member that is less air permeable than the first sheet member.

<12>

The warming device as set forth in clause <11>,
 wherein the layer containing the powder of the water absorbing resin and the air-permeable first sheet member of the enclosing material are more preferably arranged facing each other.

<13>

The warming device as set forth in any one of clauses <1> to <12>,
 wherein the heat generating element is a sheet material constituted by a base sheet and a layer of a heat generative composition provided on one surface of the base sheet,
 in the heat generating element, the ratio of the mass content of the water to the mass content of the powder of the oxidizable metal multiplied by one hundred [100×(water/powder of oxidizable metal)] is from 80 to 270, and
 the layer of the heat generative composition is obtained from a paste that contains the powder of the oxidizable metal, the powder of the carbon material, the powder of the porous material, and water.

<14>

The warming device as set forth in clause <13>,
 wherein the ratio of the mass content of the water to the mass content of the powder of the oxidizable metal multiplied by one hundred [100×(water/powder of oxidizable metal)] is preferably 80 or greater, more preferably 90 or greater, and even more preferably 110 or greater.

<15>

The warming device as set forth in clause <13> or <14>,
 wherein the ratio of the mass content of the water to the mass content of the powder of the oxidizable metal multiplied by one hundred [100×(water/powder of oxidizable metal)] is preferably 270 or less, more preferably 220 or less, and even more preferably 160 or less.

<16>

The warming device as set forth in any one of clauses <1> to <15>,
 wherein the heat generating element is constituted by a base sheet and a layer of a heat generative composition provided on one surface of the base sheet,
 the layer of the heat generative composition is obtained from a paste that contains the powder of the oxidizable metal, the powder of the carbon material, the powder of the porous material, and water,
 the warming device further comprises a layer containing a powder of a water absorbing resin, and
 the heat generative composition is disposed between the base sheet and the layer containing the powder of the water absorbing resin.

<17>

The warming device as set forth in any one of clauses <1> to <16>,
 wherein the heat generating element is constituted by a base sheet and a layer of a heat generative composition provided on one surface of the base sheet, the layer of the heat generative composition is obtained from a paste that contains the powder of the oxidizable metal, the powder of the carbon material, the powder of the porous material, and water, the warming device further includes a layer containing a powder of a water absorbing resin, and the layer containing the powder of the water absorbing resin is provided as the base sheet.

<18>

The warming device as set forth in any one of clauses <1> to <12>, wherein the heat generating element is a sheet material made of a mixture of the powder of the oxidizable metal, the powder of the carbon material, the powder of the porous material, water, and a fiber material, and in the heat generating element, the ratio of the mass content of the water to the mass content of the powder of the oxidizable metal multiplied by one hundred [100×(water/powder of oxidizable metal)] is from 30 to 80.

<19>

The warming device as set forth in clause <18>, wherein the fiber material preferably includes at least one of wood pulp, cotton, and polyester.

<20>

The warming device as set forth in clause <18> or <19>, wherein the ratio of the mass content of the water to the mass content of the powder of the oxidizable metal multiplied by one hundred [100×(water/powder of oxidizable metal)] is preferably 30 or greater, more preferably 35 or greater, and even more preferably 40 or greater.

<21>

The warming device as set forth in any one of clauses <18> to <20>, wherein the ratio of the mass content of the water to the mass content of the powder of the oxidizable metal multiplied by one hundred [100×(water/powder of oxidizable metal)] is preferably 80 or less, more preferably 70 or less, and even more preferably 60 or less.

<22>

The warming device as set forth in any one of clauses <1> to <21>, wherein the porous material has a pore diameter from 0.01 to 5 μm.

<23>

The warming device as set forth in any one of clauses <1> to <22>, wherein the porous material has a pore diameter of preferably 0.01 μm or greater, more preferably 0.02 μm or greater, even more preferably 0.05 μm or greater, yet even more preferably 0.1 μm or greater, and yet even more preferably 0.15 μm or greater.

<24>

The warming device as set forth in any one of clauses <1> to <23>, wherein the porous material has a pore diameter of preferably 5 μm or less, more preferably 1 μm or less, even more preferably 0.8 μm or less, yet even more preferably 0.5 μm or less, and yet even more preferably 0.3 μm or less.

<25>

The warming device as set forth in any one of clauses <1> to <24>, wherein the porous material is composed of a silicon-containing inorganic compound.

<26>

The warming device as set forth in any one of clauses <1> to <25>, wherein the porous material is composed of calcium silicate.

<27>

The warming device as set forth in clause <26>, wherein the calcium silicate has a pore diameter from 0.02 to 0.8 μm.

<28>

The warming device as set forth in clause <26> or <27>, wherein the calcium silicate has a pore diameter of preferably 0.02 μm or greater, more preferably 0.05 μm or greater, even more preferably 0.1 μm or greater, and yet even more preferably 0.15 μm or greater.

<29>

The warming device as set forth in any one of clauses <26> to <28>, wherein the calcium silicate has a pore diameter of preferably 0.8 μm or less, more preferably 0.5 μm or less, and even more preferably 0.3 μm or less.

<30>

The warming device as set forth in any one of clauses <26> to <29>, wherein the calcium silicate is one or two or more of a gyrolite-based compound, a wollastonite-based compound, a tobermorite-based compound, and a calcium silicate hydrate-based compound.

<31>

The warming device as set forth in any one of clauses <1> to <30>, wherein the porous material is more preferably one or two or more of gyrolite, xonotlite, and tobermorite, and the porous material is even more preferably gyrolite.

<32>

The warming device as set forth in any one of clauses <1> to <31>, wherein the amount of oil absorption of the powder of the porous material as measured according to the specification in JIS K5010-13-2 is preferably 300 mL/100 g or greater, more preferably 350 mL/100 g or greater, and even more preferably 400 mL/100 g or greater.

<33>

The warming device as set forth in any one of clauses <1> to <32>, wherein the amount of oil absorption of the powder of the porous material as measured according to the specification in JIS K5010-13-2 is preferably 900 mL/100 g or less, more preferably 800 mL/100 g or less, and even more preferably 700 mL/100 g or less.

<34>

The warming device as set forth in any one of clauses <1> to <33>, wherein particles constituting the powder of the porous material have a particle size of preferably 1 μm or greater, and more preferably 10 μm or greater, and the particle size of the particles constituting the powder of the porous material is preferably 200 μm or less, and more preferably 100 μm or less.

<35>

The warming device as set forth in any one of clauses <1> to <34>, wherein the powder of the oxidizable metal is preferably an iron powder, and the powder of the oxidizable metal is more preferably one or two or more selected from reduced iron powders and atomized iron powders.

<36>

The warming device as set forth in any one of clauses <1> to <35>,
wherein the powder of the oxidizable metal is constituted by particles having pores in their surface, and
the particles constituting the powder of the oxidizable metal preferably have a smaller pore diameter than the powder of the porous material.

<37>

The warming device as set forth in clause <36>,
wherein the pore diameter of the particles constituting the powder of the oxidizable metal is preferably 0.001 μm or greater, more preferably 0.003 μm or greater, and even more preferably 0.006 μm or greater, and
the pore diameter of the particles constituting the powder of the oxidizable metal is preferably 0.07 μm or less, more preferably 0.05 μm or less, and even more preferably 0.01 μm or less.

<38>

The warming device as set forth in any one of clauses <1> to <37>,
wherein particles constituting the powder of the oxidizable metal have a particle size of preferably 1 μm or greater, and more preferably 10 μm or greater, and
the particle size of the particles constituting the powder of the oxidizable metal is preferably 200 μm or less, and more preferably 100 μm or less.

<39>

The warming device as set forth in any one of clauses <1> to <38>,
wherein a powder of activated carbon is preferably used as the powder of the carbon material.

<40>

The warming device as set forth in any one of clauses <1> to <39>,
wherein particles constituting the powder of the carbon material have a particle size of preferably 1 μm or greater, and more preferably 10 μm or greater, and
the particle size of the particles constituting the powder of the carbon material is preferably 200 μm or less, and more preferably 100 μm or less.

<41>

The warming device as set forth in any one of clauses <1> to <40>,
wherein the heat generating element preferably contains an electrolyte.

<42>

The warming device as set forth in any one of clauses <1> to <41>, wherein the warming device includes a main body that is shaped to cover a target to be warmed when the warming device is in use and the above-described heat generating element included in the main body,
the main body includes a topsheet located on a side that is close to the target to be warmed and a backsheet located on a side that is far from the target to be warmed, and
the heat generating element is held between the topsheet and the backsheet.

<43>

The warming device as set forth in any one of clauses <1> to <42>,
wherein the warming device includes a main body that is shaped to cover user's eyes when the warming device is in use, the above-described heat generating element included in the main body, and a pair of earloop portions that are attached to the main body and can keep the user's eyes covered by the main body,
the main body includes a topsheet located on a side that is close to user's skin and a backsheet located on a side that is far from the user's skin, and
the heat generating element is held between the topsheet and the backsheet.

<44>

The warming device as set forth in clause <42>,
wherein a pressure-sensitive adhesive portion is preferably provided on a part of the region or the entire region of an outer surface of the topsheet.

<45>

The warming device as set forth in any one of clauses <1> to <42>,
wherein the warming device includes a main body that is shaped to cover at least one of the mouth and the nose of a user when the warming device is in use and the above-described heat generating element included in the main body,
the main body includes a topsheet located on a side that is close to user's skin and a backsheet located on a side that is far from the user's skin, and
the heat generating element is held between the topsheet and the backsheet.

<46>

The warming device as set forth in clause <45>, further including a pair of earloop portions that are attached to the main body and can keep at least one of the mouth and the nose of the user covered by the main body,

<47>

The warming device as set forth in clause <45>,
wherein the warming device does not include a pair of earloop portions that are attached to the main body and can keep at least one of the mouth and the nose of the user covered by the main body, and
the warming device is configured such that the main body can be held in a human hand when the warming device is in use.

<48>

The warming device as set forth in any one of clauses <42> to <47>,
wherein the air resistance of the topsheet as measured according to JIS P8117 is preferably 0.01 sec/100 mL or greater, and more preferably 0.03 sec/100 mL or greater, and
the air resistance of the backsheet as measured according to JIS P8117 is preferably 0.01 sec/100 mL or greater, and more preferably 0.03 sec/100 mL or greater.

<49>

The warming device as set forth in any one of clauses <42> to <48>,
wherein the topsheet has a basis weight of preferably 10 g/m$^2$ or greater, more preferably 30 g/m$^2$ or greater, and even more preferably 50 g/m$^2$ or greater, and
the basis weight of the topsheet is preferably 200 g/m$^2$ or less, more preferably 130 g/m$^2$ or less, and even more preferably 100 g/m$^2$ or less.

<50>

The warming device as set forth in any one of clauses <42> to <49>,
wherein it is preferred that the backsheet has a lower basis weight than the topsheet,
the basis weight of the backsheet is preferably 10 g/m$^2$ or greater, and more preferably 20 g/m$^2$ or greater, and
the basis weight of the backsheet is preferably 100 g/m$^2$ or less, and more preferably 80 g/m$^2$ or less.

<51>
The warming device as set forth in any one of clauses <42> to <50>,
 wherein the heat generating element is preferably held between the topsheet and the backsheet while being accommodated in an air-permeable enclosing material.
<52>
The warming device as set forth in clause <51>,
 wherein one surface of the enclosing material is preferably formed by an air-permeable first sheet member,
 the other surface of the enclosing material is preferably formed by a second sheet member that is less air permeable than the first sheet member,
 the first sheet member is preferably disposed facing the topsheet, and
 the second sheet member is preferably disposed facing the backsheet.
<53>
The warming device as set forth in any one of clauses <11>, <12>, and <52>,
 wherein the air resistance of the first sheet member as measured according to JIS P8117 is preferably 20 sec/100 mL or greater, more preferably 30 sec/100 mL or greater, and even more preferably 40 sec/100 mL or greater.
<54>
The warming device as set forth in any one of clauses <11>, <12>, <52>, and <53>,
 wherein the air resistance of the first sheet member as measured according to JIS P8117 is preferably 25000 sec/100 mL or less, more preferably 15000 sec/100 mL or less, and even more preferably 10000 sec/100 mL or less.
<55>
The warming device as set forth in any one of clauses <11>, <12>, and <52> to <54>,
 wherein the air resistance of the second sheet member as measured according to JIS P8117 is preferably 10000 sec/100 mL or greater, and more preferably 25000 sec/100 mL or greater, and even more preferably, the second sheet member is air impermeable.
<56>
The warming device as set forth in any one of clauses <11>, <12>, and <52> to <55>,
 wherein the water vapor transmission rate of moisture of the first sheet member as measured according to JIS Z0208 is preferably 480 g/(m²·24 h) or greater, more preferably 720 g/(m²·24 h) or greater, and even more preferably 960 g/(m²·24 h) or greater.
<57>
The warming device as set forth in any one of clauses <11>, <12>, and <52> to <56>,
 wherein the water vapor transmission rate of moisture of the first sheet member as measured according to JIS Z0208 is preferably 5000 g/(m²·24 h) or less, more preferably 4750 g/(m²·24 h) or less, and even more preferably 4500 g/(m²·24 h) or less.
<58>
The warming device as set forth in any one of clauses <11>, <12>, and <52> to <57>,
 wherein the water vapor transmission rate of moisture of the second sheet member as measured according to JIS Z0208 is preferably 480 g/(m²·24 h) or less, more preferably 240 g/(m²·24 h) or less, and even more preferably 0 g/(m²·24 h).

<59>
The warming device as set forth in any one of clauses <1> to <58>, which has a function of generating steam along with heat generation.
<60>
Use of the warming device as set forth in any one of clauses <1> to <59> as an eye mask.
<61>
Use of the warming device as set forth in any one of clauses <1> to <59> in the form of a patch.
<62>
Use of the warming device as set forth in any one of clauses <1> to <59> as a face mask.
<63>
Use of the warming device as set forth in any one of clauses <1> to <59> as a cup.

EXAMPLES

Hereinafter, the present invention will be described in further detail based on examples. However, the scope of the present invention is not limited to the examples given below. In tables below, blanks indicate "not contained".

Examples 1 to 6 and Comparative Example 1

Preparation of Coating Material

An iron powder (manufactured by DOWA IP Creation Co., Ltd., RKH3, particle size: 45 μm) was used as the powder of the oxidizable metal. An activated carbon powder (manufactured by Osaka Gas Chemicals Co., Ltd., CARBORAFFIN, particle size: 31 μm) was used as the powder of the carbon material. Gyrolite (manufactured by Tomita Pharmaceutical Co., Ltd., product name: FLORITE®, particle size: 47 μm, pore diameter D1: 0.18 μm), which is a gyrolite-based compound of a calcium silicate powder, was used as the powder of the porous material 3c. These raw materials and water, an electrolyte, and a thickener were mixed in a ratio shown in Table 1 below to obtain a paste of a heat generative composition having a viscosity of 5000 mPa·s at 25° C. as measured using a type-B viscometer.

Production of Heat Generating Element

Particles of a water absorbing resin (AQUALIC (registered trademark) CA, manufactured by Nippon Shokubai Co., Ltd.) were spread over a piece of paper made of wood pulp (basis weight: 20 g/m², manufactured by Inogami Kabushiki Kaisha) serving as a first moisture-permeable sheet so as to form a layer with a basis weight of 50 g/m². A piece of paper made of wood pulp (basis weight: 30 g/m², manufactured by Inogami Kabushiki Kaisha) serving as a second moisture-permeable sheet was laid on top of the layer of the water absorbing resin to obtain a sheet of the water absorbing resin layer.

A piece of polyethylene-laminated tissue paper (manufactured by Nittoku) was used as a base sheet. The above-described paste was applied to one surface of this sheet using a die coating method while adjusting the discharge pressure. Thus, a coated sheet product was obtained. The discharge pressure was adjusted so that the basis weight of the paste was the value shown in Table 1.

Then, 0.064 g of salt (manufactured by Otsuka Pharmaceutical Co., Ltd., pharmacopeial name: sodium chloride) was uniformly spread over the paste, and the water absorbing resin sheet was then stacked on the paste side. Thus, a stack precursor was obtained. The obtained stack precursor was then cut into a size of 49 mm×49 mm. Thus, a stack in which the water absorbing resin layer was disposed on the heat generative composition side of a coated type heat generating element was obtained.

Subsequently, the stack was sandwiched between an air-permeable first sheet member (air resistance: 1500 sec/100 mL) and an air-impermeable second sheet member each cut into a size of 63 mm×63 mm, and four sides of the sheet members were heat sealed. Thus, the heat generating element was accommodated in an enclosing material. This configuration is illustrated in FIG. 2(a).

The first sheet member of the enclosing material was disposed such that the inner surface of the first sheet member faced the outer surface of the sheet of the water absorbing resin layer. The second sheet member of the enclosing material was disposed such that the inner surface of the second sheet member faced the surface where the base sheet is present.

Finally, the heat generating element accommodated in the enclosing material was held between a topsheet made of a needle punched nonwoven fabric (basis weight: 80 g/m$^2$) and a backsheet made of an air-through nonwoven fabric (basis weight: 30 g/m$^2$), and the topsheet and the backsheet were joined to each other. Thus, an eye mask type warming device having the structure illustrated in FIGS. 4 to 7 was obtained.

The topsheet was disposed such that the inner surface of the topsheet faced the outer surface of the first sheet member of the enclosing material. The backsheet was disposed such that the inner surface of the backsheet faced the outer surface of the second sheet member of the enclosing material. This warming device was formed to generate steam along with heat generation.

Examples 7 and 8

A heat generating element, a water absorbing resin layer, and an eye mask type warming device including the heat generating element and the water absorbing resin layer were produced. The heat generating element, the water absorbing resin layer, and the eye mask type warming device had the same configurations as those of Example 1, except that a calcium silicate powder different from the calcium silicate powder used in Example 1 was used as the powder of the porous material.

The calcium silicate powder used in Example 7 was tobermorite (manufactured by Japan Insulation Co., Ltd., product name: Tobermorite, particle size: 24 µm, pore diameter D1: 0.62 µm), which is a tobermorite-based compound. The calcium silicate powder used in Example 8 was xonotlite (manufactured by Japan Insulation Co., Ltd., product name: Xonotlite, particle size: 47 µm, pore diameter D1: 0.46 µm), which is an wollastonite-based compound.

Examples 9 to 11 and Comparative Example 2

A heat generating element, a water absorbing resin layer, and a warming device were obtained in the same manner as in Example 1, except that the contents of water, the oxidizable metal, and the porous material in the heat generating element were changed as shown in Table 1 below.

Examples 12 and 13 and Comparative Example 3

The contents of water, the oxidizable metal, and the porous material in the heat generating element were changed as shown in Table 1 below.

In addition to this, the air-permeable first sheet member constituting the enclosing material was changed to a sheet member having an air resistance of 60 sec/100 mL or a sheet member having an air resistance of 4000 sec/100 mL.

The first sheet member of the enclosing material was disposed such that the inner surface of the first sheet member faced the water absorbing resin layer. The second sheet member of the enclosing material was disposed such that the inner surface of the second sheet member faced the base sheet.

The topsheet was disposed such that the inner surface of the topsheet faced the outer surface of the first sheet member of the enclosing material. The backsheet was disposed such that the inner surface of the backsheet faced the outer surface of the second sheet member of the enclosing material.

A heat generating element, a water absorbing resin layer, and a warming device were obtained in the same manner as in Example 1, except for the above-described differences.

Example 14 and Comparative Example 4

An intermediate molded body was formed by papermaking using a mixture containing the oxidizable metal, the carbon material, the porous material, and water that were used in Example 1 as well as pulp fibers (softwood kraft pulp, manufactured by Skeena, trade name "Skeena", average fiber length: 2.1 mm) serving as the fiber material. Then, an electrolyte was added to the intermediate molded body. Thus, a papermade type heat generating element having a raw material ratio shown in Table 1 below was formed.

After that, a warming device was formed in the same manner as in Example 1 using a sheet member having an air resistance of 2500 sec/100 mL as the air-permeable sheet member constituting the enclosing material.

This configuration is illustrated in FIG. 1(b).

Example 15 and Comparative Example 5

A piece of crepe paper (manufactured by Daishowa Paper Products Co., Ltd.) was used as the first moisture-permeable sheet.

A piece of polyethylene-laminated tissue paper (manufactured by Nittoku) was used as the base sheet. The above-described paste was applied to one surface of this sheet using a die coating method while adjusting the discharge pressure. Thus, a coated sheet product was obtained. The discharge pressure was adjusted so that the basis weight of the paste was the value shown in Table 2.

Then, 0.094 g of salt (manufactured by Otsuka Pharmaceutical Co., Ltd., pharmacopeial name: sodium chloride) and 0.133 g of a water absorbing polymer (sodium polyacrylate, spherical, average particle size: 300 µm, SAN-FRESH ST-500D*, manufactured by Sanyo Chemical Industries, Ltd.) were uniformly spread over the paste, and the crepe paper was then stacked on the paste side. Thus, a stack precursor was obtained. The obtained stack precursor was then cut into a size of 49 mm×49 mm. Thus, a stack in which the water absorbing resin layer was disposed on the heat generative composition side of a coated type heat generating element was obtained.

Subsequently, the stack was sandwiched between an air-permeable first sheet member (air resistance: 60 sec/100 mL) and an air-impermeable second sheet member each cut into a size of 63 mm×63 mm, and four sides of the sheet members were heat sealed. Thus, the heat generating element was accommodated in an enclosing material. This configuration is illustrated in FIG. 2(b).

The first sheet member of the enclosing material was disposed such that the inner surface of the first sheet member faced the outer surface of the sheet of the water absorbing resin layer. The second sheet member of the enclosing material was disposed such that the inner surface of the second sheet member faced the surface where the base sheet is present.

Example 16 and Comparative Example 6

Particles of a water absorbing resin (AQUALIC (registered trademark) CA, manufactured by Nippon Shokubai Co., Ltd.) were spread over a piece of paper made of wood pulp (basis weight: 20 g/m$^2$, manufactured by Inogami Kabushiki Kaisha) serving as the first moisture-permeable sheet so as to form a layer with a basis weight of 50 g/m$^2$. A piece of paper made of wood pulp (basis weight: 30 g/m$^2$, manufactured by Inogami Kabushiki Kaisha) serving as the second moisture-permeable sheet was laid on top of the layer of the water absorbing resin to obtain a sheet of the water absorbing resin layer.

A piece of polyethylene-laminated tissue paper (manufactured by Nittoku) was used as the base sheet. The above-described paste was applied to one surface of this sheet using a die coating method while adjusting the discharge pressure. Thus, a coated sheet product was obtained. The discharge pressure was adjusted so that the basis weight of the paste was the value shown in Table 2.

Then, 0.169 g of salt (manufactured by Otsuka Pharmaceutical Co., Ltd., pharmacopeial name: sodium chloride) and 0.141 g of a water absorbing polymer (sodium polyacrylate, spherical, average particle size: 300 μm, SAN-FRESH ST-500D*, manufactured by Sanyo Chemical Industries, Ltd.) were uniformly spread over the paste, and the water absorbing resin sheet was then stacked on the paste side. Thus, a stack precursor was obtained. The obtained stack precursor was then cut into a size of 49 mm×49 mm. Thus, a stack in which the water absorbing resin layer was disposed on the heat generative composition side of a coated type heat generating element was obtained.

Subsequently, the stack was sandwiched between an air-permeable first sheet member (air resistance: 60 sec/100 mL) and an air-impermeable second sheet member each cut into a size of 63 mm×63 mm, and four sides of the sheet members were heat sealed. Thus, the heat generating element was accommodated in an enclosing material. This configuration is illustrated in FIG. 2(c).

The first sheet member of the enclosing material was disposed such that the inner surface of the first sheet member faced the outer surface of the sheet of the water absorbing resin layer. The second sheet member of the enclosing material was disposed such that the inner surface of the second sheet member faced the surface where the base sheet is present.

Measurement of Integrated Amount of Sensible Heat

The integrated amount of sensible heat of each of the warming devices obtained in the examples and the comparative examples was measured according to the following method in an environment at a room temperature of 20° C. and a humidity of 50% RH.

First, as a measurement target, a warming device hermetically accommodated in an oxygen blocking pouch was prepared. The oxygen blocking pouch was opened, and one heat generating element was removed from the warming device together with the enclosing material.

Then, the removed heat generating element was placed such that the first sheet member side of the enclosing material faced outside, and a temperature sensor was placed on and fixed to a region of the second sheet member-side surface in which the heat generating element was disposed. The temperature sensor was fixed to the measurement surface using a mesh material (8-mm thick double raschel fabric made of polyester) and an SUS plate (500-g perforated plate).

Then, the temperature was measured over time using a measuring apparatus specified in JIS S4100 in a state in which the measuring apparatus was connected to the temperature sensor. The temperature was measured at intervals of 10 seconds for a total of 10 or 20 minutes, starting from the point in time when the oxygen blocking pouch was opened.

Based on a heat generation profile in which the measured temperature (° C.) was plotted on the vertical axis and the measurement time (sec) was plotted on the horizontal axis, the integral of temperatures obtained by subtracting 35° C. from the measured temperatures over a time interval in which a temperature of 35° C. or higher was measured was calculated. The calculated integral was used as the integrated amount of sensible heat (° C.·10 min or ° C.·20 min). Tables 1 and 2 below show the results.

Measurement of Amount of Steam Generation

Figure 12:
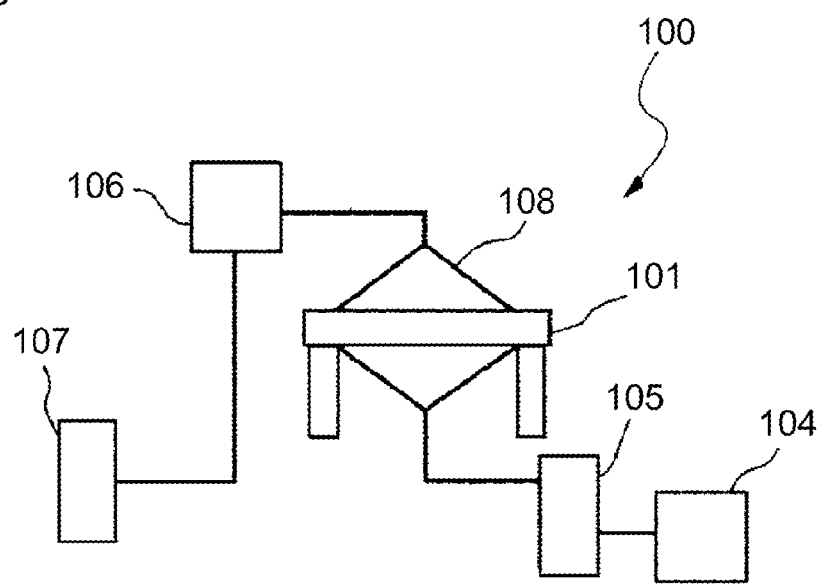
FIG. 12 is a schematic diagram of an apparatus for measuring the amount of steam generated from the warming device.

The amount of stream generated from each of the warming devices obtained in the examples and the comparative examples was measured according to the following method. More specifically, the measurement was performed using an apparatus 100 shown in FIG. 12.

First, as a measurement target, a warming device hermetically accommodated in an oxygen blocking pouch was prepared. The oxygen blocking pouch was opened, and one heat generating element was removed from the warming device together with the enclosing material.

The removed heat generating element was placed in a measurement chamber 101 such that the first sheet member side of the enclosing material faced outside, and then a weight 108 with a metal ball (mass: 4.5 g) was placed thereon. In this state, dehumidified air was caused to flow from a lower portion of the measurement chamber 101, and the difference in absolute humidity between before and after the air flowed through the measurement chamber 101 was obtained based on the temperature and the humidity measured by each of an inlet thermo-hygrometer 104 and an outlet thermo-hygrometer 106. Furthermore, the amount of steam released from the heat generating element was calculated based on the air flow rate measured by each of an inlet flowmeter 105 and an outlet flowmeter 107.

The measurement of the amount of steam generation was started at the point in time when the warming device was removed from the oxygen blocking pouch, and the total amount of steam (mg·10 min) measured for 10 minutes from the measurement start time and the total amount of steam (mg·20 min) measured for 20 minutes from the measurement start time were obtained. Tables 1 and 2 below show the results.

TABLE 1

| | | Example/Comparative Example | | | | | | | | |
|---|---|---|---|---|---|---|---|---|---|---|
| | | Com. Ex. | Ex. | Ex. | Ex. | Ex. No. | Ex. | Ex. | Ex. | Ex. |
| | | 1 | 1 | 2 | 3 | 4 | 5 | 6 | 7 | 8 |
| Form of warming device | Type of heat generating element | Coated | Coated | Coated | Coated | Coated | Coated | Coated | Coated | Coated |
| | Water vapor transmission rate of moisture of first sheet of enclosing material (g.m² · 24 hr) | 2640 | 2640 | 2640 | 2640 | 2640 | 2640 | 2640 | 2640 | 2640 |
| | Air resistance of first sheet of enclosing material (sec/100 mL) | 1500 | 1500 | 1500 | 1500 | 1500 | 1500 | 1500 | 1500 | 1500 |
| Composition of heat generating element | Water — Water | 0.819 | 0.819 | 0.819 | 0.819 | 0.819 | 0.819 | 0.818 | 0.819 | 0.819 |
| | Carbon material — Activated carbon | 0.056 | 0.056 | 0.056 | 0.056 | 0.056 | 0.056 | 0.056 | 0.056 | 0.056 |
| | Oxidizable metal — Iron power | 0.702 | 0.702 | 0.702 | 0.702 | 0.702 | 0.701 | 0.701 | 0.702 | 0.702 |
| | Porous material — Gyrolite | | 0.010 | 0.026 | 0.038 | 0.051 | 0.071 | 0.102 | | |
| | Porous material — Tobermororite | | | | | | | | 0.051 | |
| | Porous material — Xonotlite | | | | | | | | | 0.051 |
| | Fiber material — Pulp | | | | | | | | | |
| | Electrolyte — Salt | 0.064 | 0.064 | 0.064 | 0.064 | 0.064 | 0.064 | 0.064 | 0.064 | 0.064 |
| | Electrolyte — Tripotassium phosphate | 0.013 | 0.013 | 0.013 | 0.013 | 0.013 | 0.013 | 0.013 | 0.013 | 0.013 |
| | Electrolyte — 48% KOH | 0.003 | 0.003 | 0.003 | 0.003 | 0.003 | 0.003 | 0.003 | 0.003 | 0.003 |
| | Thickener — Xanthan gum | 0.002 | 0.002 | 0.002 | 0.002 | 0.002 | 0.002 | 0.002 | 0.002 | 0.002 |
| Content ratio of raw materials in heat generating element (mass ratio × 100) | Water/Oxidizable metal | 116.7 | 116.7 | 116.7 | 116.7 | 116.7 | 116.7 | 116.7 | 116.7 | 116.7 |
| | Porous material/oxidizable | 0.0 | 1.5 | 3.6 | 5.5 | 7.3 | 10.2 | 14.5 | 7.3 | 7.3 |
| | Porous material/Water | 0.0 | 1.2 | 3.1 | 4.7 | 6.2 | 8.7 | 12.5 | 6.2 | 6.2 |
| Evaluation of warming device | Integrated amount of sensible heat measured for 10 minutes (° C. · 10 min) | 1160 | 1321 | 1627 | 1678 | 1699 | 1478 | 1247 | 1609 | 1473 |
| | Integrated amount of sensible heat measured for 20 minutes (° C. · 20 min) | 2302 | 2772 | 3255 | 3319 | 3399 | 2944 | 2853 | 3079 | 2908 |
| | Amount of steam generation measured for 10 minutes (mg · 10 min) | 105 | 144 | 180 | 189 | 232 | 211 | 233 | 231 | 209 |
| | Amount of steam generation measured for 20 minutes (mg · 20 min) | 182 | 253 | 278 | 285 | 346 | 327 | 399 | 342 | 324 |

TABLE 1-continued

| | | Example/Comparative Example | | | | | | | | |
|---|---|---|---|---|---|---|---|---|---|---|
| | | Com. Ex. | Ex. | Ex. | Ex. | Com. Ex. | Ex. | Ex. | Com. Ex. | Ex. |
| | | No. | | | | | | | | |
| | | 2 | 9 | 10 | 11 | 3 | 12 | 13 | 4 | 14 |
| Form of warming device | Type of heat generating element | Coated | Coated | Coated | Coated | Coated | Coated | Coated | Paper-made | Paper-made |
| | Water vapor transmission rate of moisture of first sheet of enclosing material (g.m$^2$ · 24 hr) | 2640 | 2640 | 2640 | 2640 | 4000 | 4000 | 1320 | 1920 | 1920 |
| | Air resistance of first sheet of enclosing material (sec/100 mL) | 1500 | 1500 | 1500 | 1500 | 60 | 60 | 4000 | 2500 | 2500 |
| Composition of heat generating element | Water — Water | 0.441 | 0.691 | 0.946 | 1.202 | 0.788 | 0.789 | 0.761 | 0.429 | 0.429 |
| | Carbon material — Activated carbon | 0.057 | 0.056 | 0.056 | 0.056 | 0.030 | 0.030 | 0.084 | 0.094 | 0.094 |
| | Oxidizable metal — Iron power | 0.709 | 0.701 | 0.702 | 0.702 | 0.380 | 0.380 | 0.529 | 0.529 | 0.870 |
| | Porous material — Gyrolite Tobermororite Xonotlite | | 0.043 | 0.059 | 0.075 | | 0.049 | 0.029 | | 0.050 |
| | Fiber material — Pulp | | | | | | | | 0.084 | 0.084 |
| | Electrolyte — Salt | 0.034 | 0.054 | 0.074 | 0.094 | 0.061 | 0.061 | 0.067 | 0.023 | 0.023 |
| | Tripotassium phosphate | 0.014 | 0.013 | 0.013 | 0.013 | 0.007 | 0.007 | 0.019 | 0.000 | 0.000 |
| | 48% KOH | 0.003 | 0.003 | 0.003 | 0.003 | 0.002 | 0.002 | 0.009 | 0.000 | 0.000 |
| | Thickener — Xanthan gum | 0.002 | 0.002 | 0.002 | 0.002 | 0.001 | 0.001 | 0.002 | 0.000 | 0.000 |
| Content ratio of raw materials in heat generating element (mass ratio × 100) | Water/Oxidizable metal | 62.2 | 98.5 | 134.9 | 171.3 | 207.6 | 207.6 | 144.0 | 49.3 | 49.3 |
| | Porous material/oxidizable | 0.0 | 6.1 | 8.4 | 10.7 | 0.0 | 12.9 | 5.5 | 0.0 | 5.7 |
| | Porous material/Water | 0.0 | 6.2 | 6.2 | 6.2 | 0.0 | 6.2 | 3.8 | 0.0 | 11.6 |
| Evaluation of warming device | Integrated amount of sensible heat measured for 10 minutes (° C. · 10 min) | 1419 | 1539 | 1632 | 1222 | 612 | 1177 | 1334 | 1376 | 1451 |
| | Integrated amount of sensible heat measured for 20 minutes (° C. · 20 min) | 2146 | 2742 | 3742 | 3066 | 1079 | 2012 | 3120 | 2060 | 2535 |
| | Amount of steam generation measured for 10 minutes (mg · 10 min) | 128 | 207 | 170 | 87 | 105 | 172 | 83 | 73 | 100 |
| | Amount of steam generation measured for 20 minutes (mg · 20 min) | 186 | 295 | 338 | 281 | 170 | 288 | 138 | 105 | 140 |

TABLE 2

|  |  | Example/Comparative Example | | | |
|---|---|---|---|---|---|
|  |  | Ex. | Com. Ex. | Ex. | Com. Ex. |
|  |  | No. | | | |
|  |  | 15 | 5 | 16 | 6 |
| Form of warming device | Type of heat generating element | Coated | Coated | Coated | Coated |
|  | Water vapor transmission rate of moisture of first sheet of enclosing material (g/m² · 24 hr) | 4000 | 4000 | 4000 | 4000 |
|  | Air resistance of first sheet of enclosing material (sec/100 mL) | 60 | 60 | 60 | 60 |
| Composition of heat generating element (g) | Water — Water | 1.063 | 1.063 | 1.913 | 1.913 |
|  | Carbon material — Activated carbon | 0.118 | 0.118 | 0.212 | 0.212 |
|  | Oxidizable metal — Iron powder | 0.738 | 0.738 | 1.328 | 1.328 |
|  | Porous material — Gyrolite | 0.040 |  | 0.072 |  |
|  | Porous material — Tobermorite |  |  |  |  |
|  | Porous material — Xonotlite |  |  |  |  |
|  | Fiber material — Pulp |  |  |  |  |
|  | Electrolyte — Salt | 0.094 | 0.094 | 0.169 | 0.169 |
|  | Electrolyte — Tripotassium phosphate | 0.026 | 0.026 | 0.047 | 0.047 |
|  | Electrolyte — 48% KOH | 0.013 | 0.013 | 0.023 | 0.023 |
|  | Thickener — Xanthan gum | 0.003 | 0.003 | 0.005 | 0.005 |
| Content ratio of raw materials in heat generating element (mass ratio × 100) | Water/Oxidizable metal | 144.0 | 144.0 | 144.0 | 144.0 |
|  | Porous material/Oxidizable metal | 5.5 | 5.5 | 5.5 | 5.5 |
|  | Porous material/Water | 3.8 | 3.8 | 3.8 | 3.8 |
| Evaluation of warming device | Integrated amount of sensible heat measured for 10 minutes (° C. · 10 min) | 1113 | 450 | 1578 | 1169 |
|  | Integrated amount of sensible heat measured for 20 minutes (° C. · 20 min) | 2404 | 1607 | 3743 | 2983 |
|  | Amount of steam generation measured for 10 minutes (mg · 10 min) | 297 | 122 | 537 | 380 |
|  | Amount of steam generation measured for 20 minutes (mg · 20 min) | 570 | 318 | 1033 | 925 |

As shown in Tables 1 and 2, it can be seen that, as a result of the warming devices of the examples each including the heat generating element in which the powder of the porous material was contained and at least one of the content ratio between the oxidizable metal and water, the content ratio between the water and the porous material, and the content ratio between the oxidizable metal and the porous material satisfied a specific relationship, the warming devices of the examples had a higher integrated amount of sensible heat and superior heat generation characteristics, compared with the warming devices of the comparative examples, even though the oxidizable metal contents in the warming devices were substantially equal. In addition, it can be seen that, due to this, the warming devices of the examples generated a markedly larger amount of steam. Furthermore, it can be seen that, even when the heat generating element was accommodated in the enclosing material, the warming devices of the examples had superior heat generation characteristics and generated a large amount of steam, irrespective of the fiber sheet used.

Therefore, it is found that, according to the warming device of the present disclosure, a warming device having excellent heat generation characteristics can be produced while suppressing the production cost, without increasing the content of the oxidizable metal, which is expensive.

INDUSTRIAL APPLICABILITY

A warming device that has excellent heat generation characteristics and generates a large amount of steam is provided while suppressing the production cost.

The invention claimed is:

1. A warming device comprising a heat generating element that contains a powder of an oxidizable metal, a powder of a carbon material, water, and a powder of a porous material other than the oxidizable metal and the carbon material,
wherein the heat generating element is a sheet material, and
in the heat generating element, a ratio of the mass content of the water to the mass content of the powder of the oxidizable metal multiplied by one hundred [100×(water/powder of oxidizable metal)] is from 30 to 270.

2. A warming device comprising a heat generating element that contains a powder of an oxidizable metal, a powder of a carbon material, water, and a powder of a porous material other than the oxidizable metal and the carbon material,
wherein the heat generating element is a sheet material, and
in the heat generating element, a ratio of the mass content of the powder of the porous material to the mass content of the powder of the oxidizable metal multiplied by one hundred [100×(powder of porous material/powder of oxidizable metal)] is from 1 to 25.

3. A warming device comprising a heat generating element that contains a powder of an oxidizable metal, a powder of a carbon material, water, and a powder of a porous material other than the oxidizable metal and the carbon material,
wherein the heat generating element is a sheet material, and in the heat generating element, a ratio of the mass content of the powder of the porous material to the mass content of the water multiplied by one hundred [100× (powder of porous material/water)] is from 1 to 30.

4. The warming device according to claim 1,
wherein the heat generating element is accommodated in an air-permeable enclosing material, and
a layer containing a powder of a water absorbing resin is disposed between the heat generating element and the enclosing material.

5. The warming device according to claim 4, wherein the layer is formed by sandwiching the powder of the water absorbing resin between two moisture-permeable sheets.

6. The warming device according to claim 1,
wherein the sheet material has a base sheet and a layer of a heat generative composition provided on one surface of the base sheet,
in the heat generating element, a ratio of the mass content of the water to the mass content of the powder of the oxidizable metal multiplied by one hundred [100× (water/powder of oxidizable metal)] is from 80 to 270, and
the layer of the heat generative composition is obtained from a paste that contains the powder of the oxidizable metal, the powder of the carbon material, the powder of the porous material, and water.

7. The warming device according to claim 1,
wherein the sheet material is made of a mixture of the powder of the oxidizable metal, the powder of the carbon material, the powder of the porous material, water, and a fiber material, and
in the heat generating element, a ratio of the mass content of the water to the mass content of the powder of the oxidizable metal multiplied by one hundred [100× (water/powder of oxidizable metal)] is from 30 to 80.

8. The warming device according to claim 1,
wherein the sheet material has a base sheet and a layer of a heat generative composition provided on one surface of the base sheet,
the layer of the heat generative composition is obtained from a paste that contains the powder of the oxidizable metal, the powder of the carbon material, the powder of the porous material, and water,
the warming device further comprises a layer containing a powder of a water absorbing resin, and
the heat generative composition is disposed between the base sheet and the layer containing the powder of the water absorbing resin.

9. The warming device according to claim 1, wherein the porous material has a pore diameter from 0.01 to 5 μm.

10. The warming device according to claim 1, wherein the porous material contains a silicon-containing inorganic compound.

11. The warming device according to claim 10, wherein the porous material is composed of calcium silicate.

12. The warming device according to claim 11, wherein the calcium silicate has a pore diameter from 0.02 to 0.8 μm.

13. The warming device according to claim 1, comprising:
a main body that is shaped to cover a user's eyes when the warming device is in use;
wherein the heat generating element is included in the main body; and
a pair of earloop portions that are attached to the main body and can keep the user's eyes covered by the main body,
wherein the main body includes a topsheet located on a side that is close to the user's skin and a backsheet located on a side that is far from the user's skin, and
the heat generating element is held between the topsheet and the backsheet.

14. A method of generating steam and heat, comprising: applying the warming device according to claim 1.

15. A warming device comprising a heat generating element that contains a powder of an oxidizable metal, a powder of a carbon material, water, and calcium silicate,
wherein the heat generating element is a sheet material, and
in the heat generating element, a ratio of the mass content of the water to the mass content of the powder of the oxidizable metal multiplied by one hundred [100× (water/powder of oxidizable metal)] is from 30 to 270.

* * * * *